US012806347B2

(12) United States Patent
Connolly et al.

(10) Patent No.: US 12,806,347 B2
(45) Date of Patent: Nov. 24, 2026

(54) VIBRATING APERTURE PLATE NEBULIZER

(71) Applicant: STAMFORD DEVICES LIMITED, Galway (IE)

(72) Inventors: Diarmuid Connolly, Galway (IE); Colm Carmody, Galway (IE); Finbarr Maguire, County Clare (IE); Aidan Duffy, Galway (IE)

(73) Assignee: STAMFORD DEVICES LIMITED, Galway (IE)

( * ) Notice: Subject to any disclaimer, the term of this patent is extended or adjusted under 35 U.S.C. 154(b) by 1193 days.

(21) Appl. No.: 17/756,730

(22) PCT Filed: Mar. 22, 2021

(86) PCT No.: PCT/EP2021/057304
§ 371 (c)(1),
(2) Date: Jun. 1, 2022

(87) PCT Pub. No.: WO2021/191160
PCT Pub. Date: Sep. 30, 2021

(65) Prior Publication Data

US 2023/0001107 A1 Jan. 5, 2023

(30) Foreign Application Priority Data

Mar. 24, 2020 (EP) .................................... 20165404
Mar. 24, 2020 (EP) .................................... 20165407
(Continued)

(51) Int. Cl.
*A61M 11/00* (2006.01)
*B05B 17/00* (2006.01)

(52) U.S. Cl.
CPC ....... *A61M 11/005* (2013.01); *B05B 17/0646* (2013.01); *A61M 2207/10* (2013.01)

(58) Field of Classification Search
CPC . A61M 11/005; A61M 15/0085; B05B 17/06; B05B 17/0646; B05B 17/0638
See application file for complete search history.

(56) References Cited

U.S. PATENT DOCUMENTS 11,684,943 B2 * 6/2023 Lin .................... B05B 17/0623 128/200.16
2006/0207591 A1 * 9/2006 Gallem .............. B05B 17/0646 128/200.22
(Continued)

FOREIGN PATENT DOCUMENTS

EP 3560604 A1 10/2019
EP 4035780 A1 8/2022
(Continued)

OTHER PUBLICATIONS

International Search Report and Written Opinion issued in International Application PCT/EP2021/051304 on Jun. 24, 2021 (15 pages).
(Continued)

*Primary Examiner* — Douglas Y Sul
(74) *Attorney, Agent, or Firm* — Bookoff McAndrews, PLLC

(57) ABSTRACT

A nebulizer has an aerosol generator mounted in a housing, and has a vibratable aperture plate mounted to an annular support and to which is attached a vibration generator piezo. A downstream annular resilient seal is mounted between the housing and the washer on a side of the aperture plate opposed to the liquid supply reservoir. An upstream resilient seal is in the form of a gasket and is mounted between the washer and the housing reservoir, and has an opening forming part of a throat over the aperture plate. The gasket has a washer-shaped body extending radially from a downstream-extending rim adjacent the aperture plate. There are two upwardly-directed ridges for engagement with a housing surface, and the gasket is configured so that when under
(Continued)

axial compression the opening internal surface is tapered inwardly in a flow direction to form a funnel shape.

14 Claims, 18 Drawing Sheets

(30) Foreign Application Priority Data

Mar. 24, 2020 (EP) .................................... 20165409
Mar. 24, 2020 (EP) .................................... 20165410

(56) References Cited

U.S. PATENT DOCUMENTS

| | | | | |
|---|---|---|---|---|
| 2012/0111970 | A1* | 5/2012 | Hogan | B05B 17/0646 239/102.2 |
| 2015/0238993 | A1 | 8/2015 | Hsieh et al. | |
| 2015/0306623 | A1* | 10/2015 | Kawano | B05B 17/0684 239/102.2 |
| 2015/0375252 | A1 | 12/2015 | Lee et al. | |
| 2017/0043106 | A1* | 2/2017 | Hyland | A61M 16/0833 |
| 2017/0119059 | A1* | 5/2017 | Zuber | B05B 17/0607 |
| 2018/0178240 | A1* | 6/2018 | Anzenberger | B05B 17/0646 |
| 2018/0193869 | A1 | 7/2018 | Biette | |
| 2019/0038851 | A1* | 2/2019 | Hijlkema | A61M 11/005 |

FOREIGN PATENT DOCUMENTS

| | | | |
|---|---|---|---|
| WO | 2012046220 | A1 | 4/2012 |
| WO | 2012092163 | A1 | 7/2012 |
| WO | 2013186031 | A2 | 12/2013 |
| WO | 2014133273 | A1 | 9/2014 |
| WO | 2016151029 | A1 | 9/2016 |
| WO | 2019115221 | A1 | 6/2019 |
| WO | 2019214281 | A1 | 11/2019 |

OTHER PUBLICATIONS

European Search Report in corresponding EP Application No. 25197335, dated Nov. 7, 2025, (10 pages).

* cited by examiner

VIBRATING APERTURE PLATE NEBULIZER

CROSS-REFERENCE TO RELATED APPLICATIONS

This patent application is the U.S. National Stage entry under 35 U.S.C. § 371 of International Patent Application No. PCT/EP2021/057304, filed on Mar. 22, 2021, which claims the benefit of priority to European Patent Application No. 20165410.0, filed on Mar. 24, 2020, European Patent Application No. 20165407.6, filed on Mar. 24, 2020, European Patent Application No. 20165409.2, filed on Mar. 24, 2020, and European Patent Application No. 20165404.3, filed on Mar. 24, 2020.

INTRODUCTION

The invention relates to nebulizers of the type having a vibrating aperture plate aerosol generator.

Our prior specification WO2012046220A describes an aerosol generator with a funnel-shaped housing top part forming a reservoir, inclined to the axis of a tubular lower part. An aperture plate ("AP") is attached to a washer-shaped support on which there is an annular piezoelectric vibration generator. Power is provided via pins to the top of the piezo directly and via the washer to the bottom of the piezo. Such a nebulizer works very effectively.

However, vibrating aperture plate nebulisers naturally tend to ingest air through the centre of the aperture plate when nebulising. These bubbles have a size in the micrometre range and have the potential to migrate to the walls of the nebuliser throat over the aperture plate. Here they may stagnate, coalesce and form a larger air bubble. These larger air bubbles can reduce or interrupt nebulization. Sometimes it helps to tap the nebuliser to release the air bubble and recommence nebulisation.

Our prior published patent specification WO2016151029A describes an approach to bubble prevention which involves providing physical features in the interior reservoir surface, to physically prevent bubbles from forming to be large. EP3560604 (Microbase) describes an aerosol generator with an inner gasket on an inner edge of a washer-shaped piezo element. WO2014/133273 (KTMED) describes a liquid medicine inhaler. US2015/0375252 (DELBio, INC) describes a spraying device, WO2019/214281 (TAIANDALU) describes a medical nebulizer, and US2018/0193869 (United Therapeutics Corp) describes an adjustable aerosol delivery device.

The present invention is directed towards achieving improvements in efficiency and consistency of conversion of the liquid into aerosol and/or more efficient robotic manufacture of the nebulizer.

SUMMARY OF THE INVENTION

We describe a nebulizer comprising a liquid supply reservoir, an aerosol outlet, and an aerosol generator comprising:

- an annular support supporting the aperture plate,
- a vibration generator attached to the annular support,
- a power conductor for transferring power to the vibration generator,
- a downstream resilient seal mounted between a housing and the annular support on a side
- of the aperture plate opposed to the liquid supply reservoir, and

- an upstream resilient seal mounted between the annular support and the housing reservoir,
- and having an opening forming part of a throat over the aperture plate.

In one example, the upstream resilient seal comprises a gasket having a body and a downstream-extending rim adjacent the opening, the body extending radially from said rim in a substantially annular shape. In one example, the gasket comprises at least one upwardly-directed ridge for engagement with a housing surface. Preferably, there are two or more upwardly-directed ridges, and preferably at least one of said ridges is circular in plan, preferably concentric. In one example, the ridges have a height in the range of 0.1 mm and 0.5 mm, and the downstream-extending rim has a depth relative to the gasket body in the range of 0.5 mm and 1.1 mm.

In one example, the upstream resilient seal is configured so that when under axial compression the opening has an internal surface which is tapered inwardly in a flow direction to form a funnel shape at the throat. In one example, the upstream resilient seal opening internal surface forms a continuation of the housing reservoir internal surface when the seal is under compression.

In various examples, the gasket body overlies at least part of the annular support and preferably also overlies at least part of the vibration generator. In one example, the gasket overlies and is in contact with an upper surface of the vibration generator, said vibration generator being mounted to atop (upstream) surface of the support.

In various examples, the housing comprises a retainer which is engageable with the aerosol outlet, and the aerosol generator is supported by the retainer. Preferably, the retainer is snap-fitted within the aerosol outlet. Preferably, engagement between the retainer and the aerosol outlet is between toes of the retainer engaging in recesses of the housing, and engagement being assisted by compression and axial reactive force of the resilient seals. Preferably, the retainer comprises an annular seat for the downstream resilient seal; and wherein the support, the aperture plate, the vibration generator, and the gasket are supported over said downstream resilient seal. In one example, the retainer forms an annular seat for the upstream resilient seal, and preferably In various examples, the throat has an area in the plane of the aperture plate of at least 18 $mm^2$ preferably at least 20 $mm^2$, more preferably at least 25 $mm^2$, more preferably at least 30 $mm^2$, and more preferably in the range of about 32 $mm^2$ to 40 $mm^2$. In one example, the throat has an area in the plane of the aperture plate of at least twice the vibratable area of the aperture plate.

In one example, the upstream resilient seal opening has a diameter when in the housing and compressed in excess of 5 mm, and preferably in excess of 5.5 mm, and more preferably in excess of 6.0 mm. In one example, the upstream resilient seal opening has an axial dimension in the range of 1.8 mm and 3.0 mm, and preferably in excess of 2.0 mm.

In one example, the nebulizer comprises a pair of conducting spring pins for driving the vibration generator, and one or both of said pins extends through an aperture in the gasket.

In one example, the upstream resilient seal is of medical grade liquid silicone rubber supplied as two component compounds which are mixed together and injected into a hot mould to cure. In various examples, the upstream resilient seal has a Shore hardness in the range of 20 to 80 Shore A, preferably 30 to 60 Shore A In various examples, the gasket comprises a plurality of downstream ridges. In various examples, the vibration generator is mounted to an upstream surface of the support, and at least one downstream-extending ridge extends around an outer periphery the vibration generator.

In various examples, the gasket extends in the radial direction to form a resilient seal between plastics housing parts, and the gasket may extend in the radial direction to completely overlie the vibration generator; and in some examples the gasket extends in the radial direction to completely overlie the support; and it may extend in the radial direction to engage the housing at its outer edge.

In various examples, the upstream resilient seal has on at least some of its exposed surface a surface roughness Ra value in the range of 1.64 m to 3.24 m.

In various examples, the upstream resilient seal has on at least some of its exposed surface a hydrophilic coating.

In various examples, the retainer comprises at least two opposed ramps for guiding insertion of the retainer into the housing.

We also describe a method of manufacturing a nebulizer of any of the examples with a retainer, the method comprising mounting the aerosol generator to the retainer and moving robotically the retainer towards the housing reservoir until the retainer snap fits into position onto the housing, being retained by axial resilient reactive forces of the upstream seal (48) and the downstream seal.

In various examples, the retainer comprises at least two opposed ramps for guiding insertion of the retainer into the housing and said action of moving the retainer towards the housing reservoir is guided for alignment by said ramps.

We also describe a nebulizer comprising: a housing, a liquid supply reservoir, an aerosol outlet, an aerosol generator mounted in the housing and comprising:

a vibratable aperture plate, an annular support supporting the aperture plate, a vibration generator attached to the annular support, a power conductor for transferring power to the vibration generator, a downstream annular resilient seal mounted between the housing and the annular support on a side of the aperture plate, and an upstream resilient seal mounted between the annular support and the housing, and having an opening with an exposed surface forming part of a throat over the aperture plate, and at least some of said surface is roughened.

In various examples, at least some of said exposed surface has a roughness average in the range of 1.6 μm to 3.2 μm. In various examples, said exposed surface forms a funnel shape at the throat.

In various examples, the housing reservoir forms a bend to widen from the throat, and said bend extends at an angle in excess of 40° from axial. In various examples, the aperture plate has apertures with a diameter in the range of 2 μm and 6 μm. In various examples, the axial distance from the plane of a rim of the aperture plate and the bend is in the range of 1.8 mm and 3.0 mm. In various examples, the axial dimension of the seal at the throat is in the range of I.S m and 3.0 mm.

ADDITIONAL STATEMENTS a housing, a liquid supply reservoir formed by the housing, an aerosol outlet in the housing, an aerosol generator mounted in the housing and comprising:

a vibratable aperture plate, an annular support supporting the aperture plate, a vibration generator attached to the annular support, a power conductor for transferring power to the vibration generator, a downstream annular resilient seal mounted between the housing and the annular support on a downstream side of the aperture plate opposed to the liquid supply reservoir, and an upstream resilient seal mounted between the annular support and the housing reservoir, and having an opening forming part of a throat over the aperture plate.

Preferably, the upstream resilient seal is in the form of a gasket having a body and a downstream-extending rim adjacent the opening, the body extending radially from said rim in a substantially annular shape. Preferably, the gasket comprises at least one upwardly-directed ridge for engagement with a housing surface. Preferably, there are two or more upwardly-directed ridges. Preferably, at least one of said ridges is circular in plan, preferably concentric.

Preferably, the ridges have a height (relative to the gasket body) in the range of O. I mm and 0.5 mm, and the downstream-extending rim has a height (relative to the gasket body) in the range of O.5 mm and I. I mm. Preferably, the gasket is configured so that when under axial compression the opening internal surface is tapered inwardly in a flow direction to form a funnel shape.

Preferably, some of the opening internal surface is formed by the downstream ridge. Preferably, the gasket body overlies at least part of the annular support.

Preferably, the gasket body overlies at least part of the vibration generator.

Preferably, the gasket overlies and is in contact with an upper surface of the vibration generator, said vibration generator being mounted to a top surface of the support.

Preferably, the housing comprises a retainer which is engageable with an aerosol outlet part of the chamber. Preferably, the retainer is snap-fitted within the aerosol outlet, with engagement between the retainer and the aerosol outlet being assisted by compression and axial reactive force of the upstream and downstream resilient seals.

Preferably, the retainer comprises an annular seat for the downstream resilient seal, and wherein the support, the aperture plate, the vibration generator, and the gasket are supported over said lower resilient seal. Preferably, the retainer forms an annular seat for the gasket.

Preferably, the retainer comprises circumferential and axially-directed tabs forming side walls of said gasket seat.

Preferably, the throat has an area in the plane of the AP of at least 18 $mm^2$, more preferably at least 20 $mm^2$, more preferably at least 25 $mm^2$, more preferably at least 30 $mm^2$.

In one preferred example, the throat has an area in the plane of the AP in the range of about 32 $mm^2$ to 40 $mm^2$.

Preferably, the throat has an area in the plane of the AP of at least twice the active area of the aperture plate.

Preferably, the gasket opening has a diameter when in the housing and compressed in excess of 5 mm, and preferably in excess of 5.5 mm, and more preferably in excess of 6.0 mm.

Preferably, the gasket opening has an axial dimension in excess of 2.0 mm. Preferably, the nebulizer comprises a pair of conducing spring pins for driving the vibration generator, and one or both of said pins extends through an aperture in the gasket.

Preferably, the gasket is of medical grade liquid silicone rubber supplied as two component compounds which are mixed together and injected into a hot mould to cure.

Preferably, the gasket has a Shore hardness in the range of 20 to 80 Shore A, more preferably in the range of 30 to 60 Shore A In one preferred example, the gasket comprises a plurality of downstream ridges.

In one preferred example, the vibration generator is mounted to an upstream surface of the support, and at least one downstream-extending ridge extends around an outer periphery the vibration generator.

In one preferred example, the gasket extends in the radial direction to form a resilient seal between plastics housing parts.

In one preferred example, the gasket extends in the radial direction to completely overlie the vibration generator.

In one preferred example, the gasket extends in the radial direction to completely overlie the support.

In one preferred example, the gasket extends in the radial direction to engage the housing at its outer edge.

In one preferred example, the gasket has on at least some of its exposed surface a surface roughness in the range of 1.6 μm to 3.2 μm.

In one preferred example, the gasket has on at least some of its exposed surface a hydrophilic coating.

We also describe a method of manufacturing a nebulizer of any described example, the method comprising mounting the aerosol generator to the retainer and moving robotically the retainer towards the housing reservoir until the retainer snap fits into position onto the housing, being retained by axial resilient reactive forces of the upstream and downstream seals.

DETAILED DESCRIPTION OF THE INVENTION

The invention will be more clearly understood from the following description of some embodiments thereof, given by way of example only with reference to the accompanying drawings in which.

Figure 5:
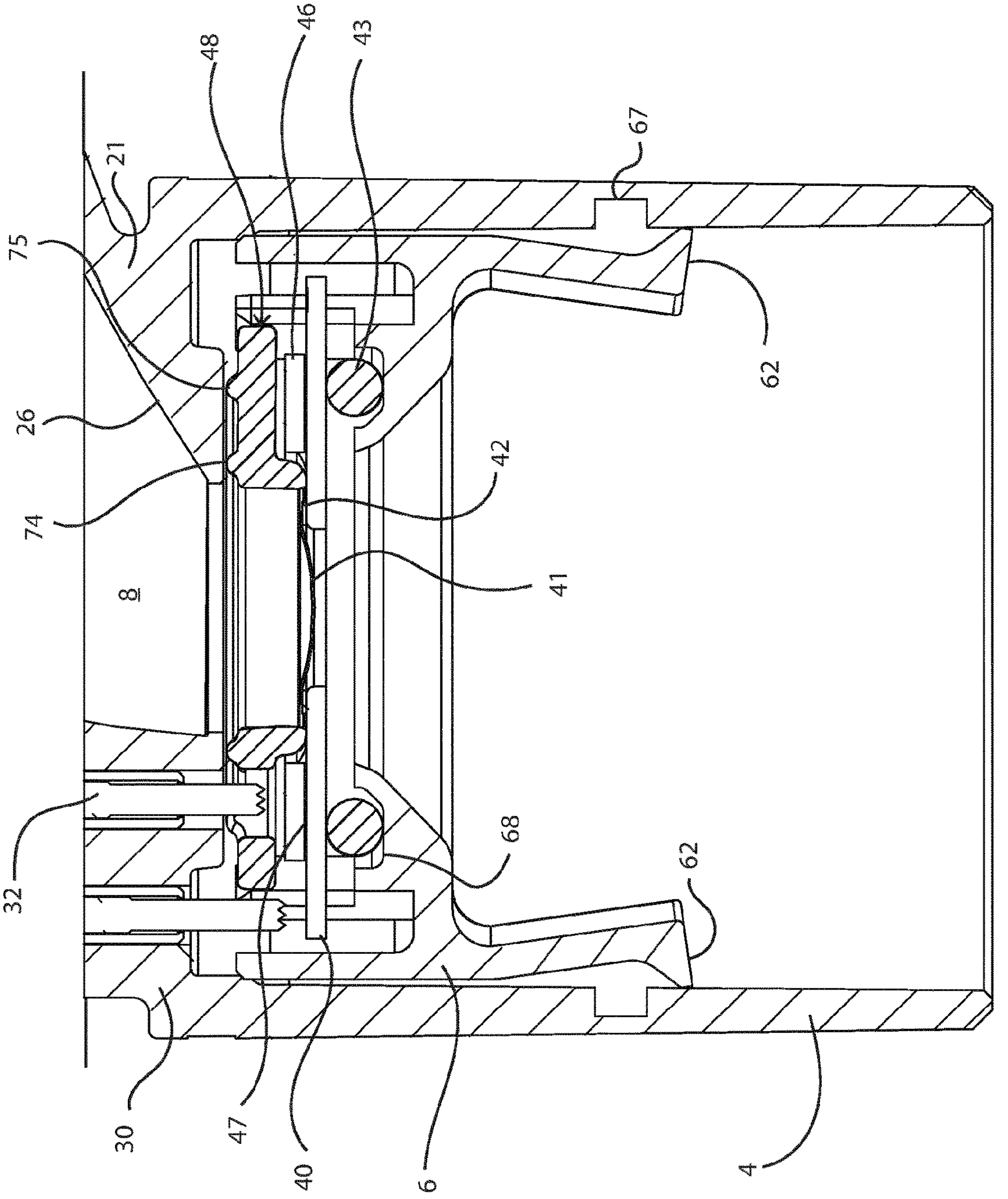
Figure 6:
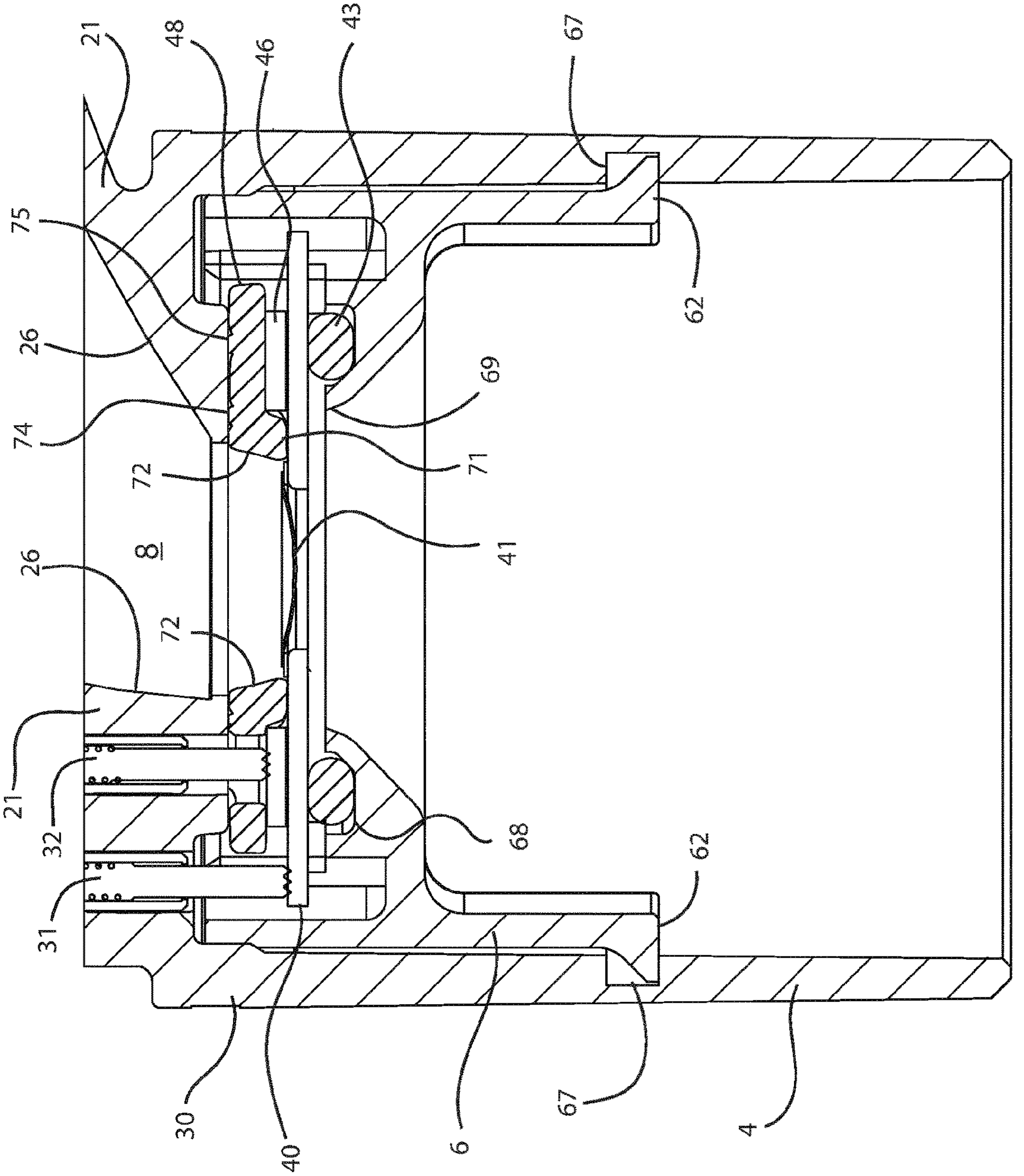
Figure 7:
Figure 8:
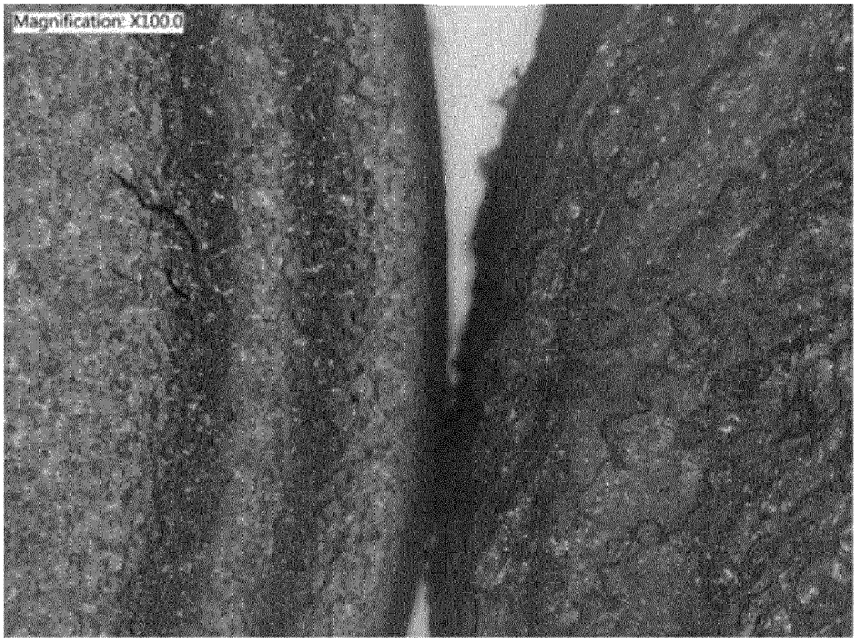

(a) perspective view, (b) cross-sectional view through the gasket, showing an aperture for a conducting pin, (c) top plan view, and (d) bottom plan view;

FIG. 5 is a cross sectional view during assembly, before the conducting pins make contact; and FIG. 6 is a similar view to that of FIG. 5, in this case after the pins are contacting the piezoelectric vibration generator (“piezo”) and the support washer, with the retainer snap-fitted into place;

FIG. 7 is an image showing bubble formation on the aperture plate, especially around the rim where it is attached by brazing to the support washer, and FIG. 8 is a pair of magnified images showing the surfaces of two gaskets, which are configured to minimize bubble retention and enlargement at the gasket surface.

Figure 9:
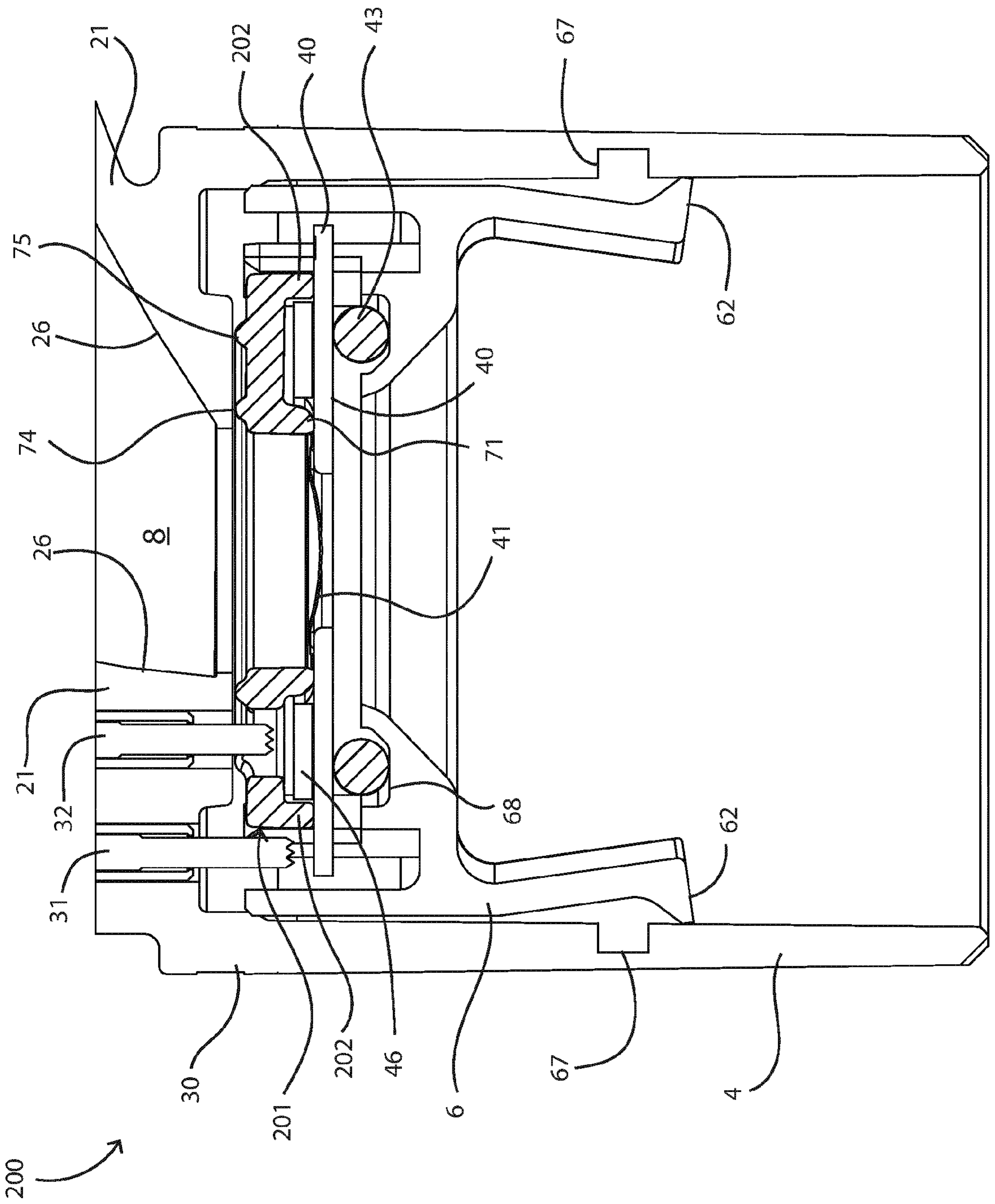
Figure 10:
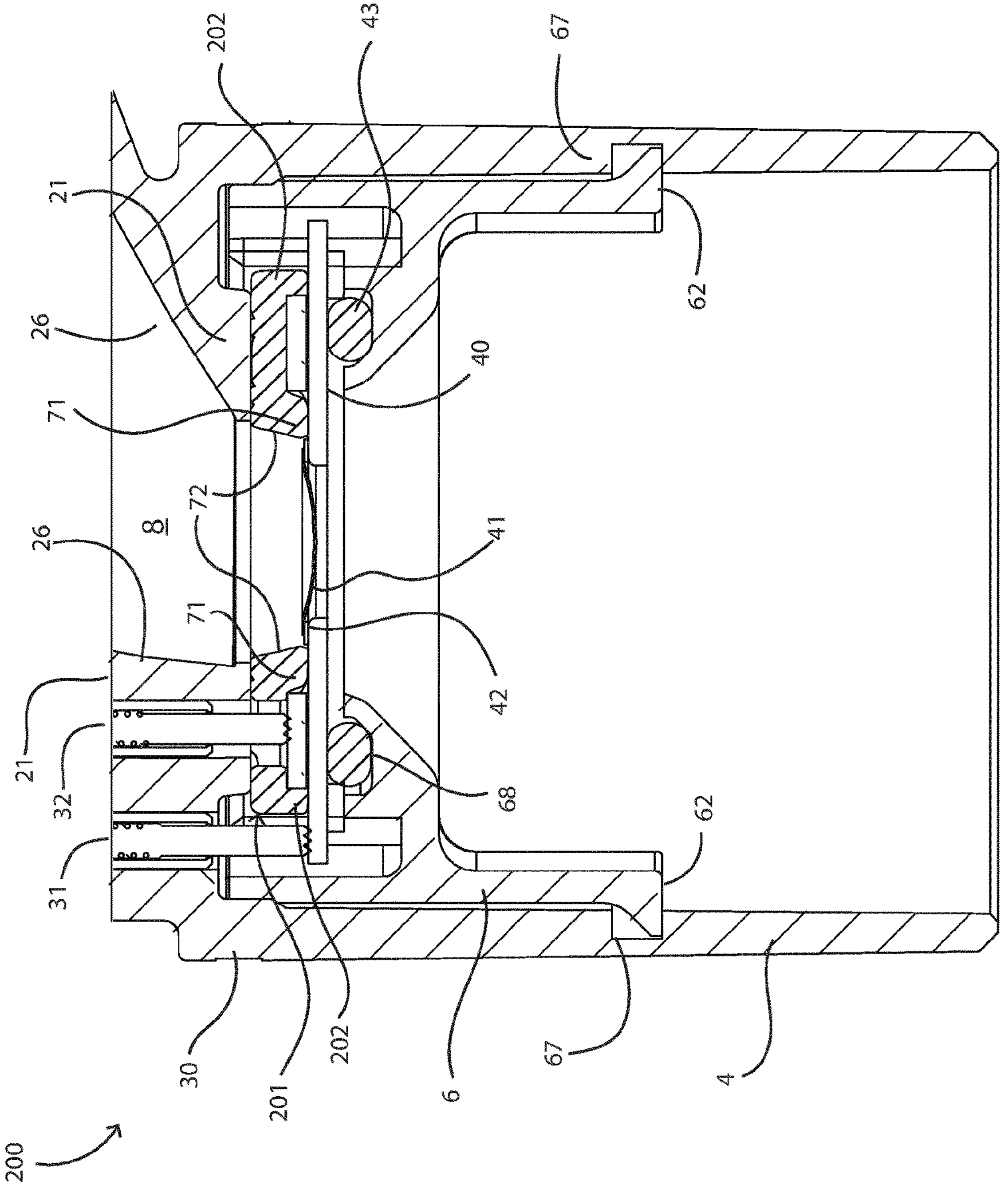
Figure 11:
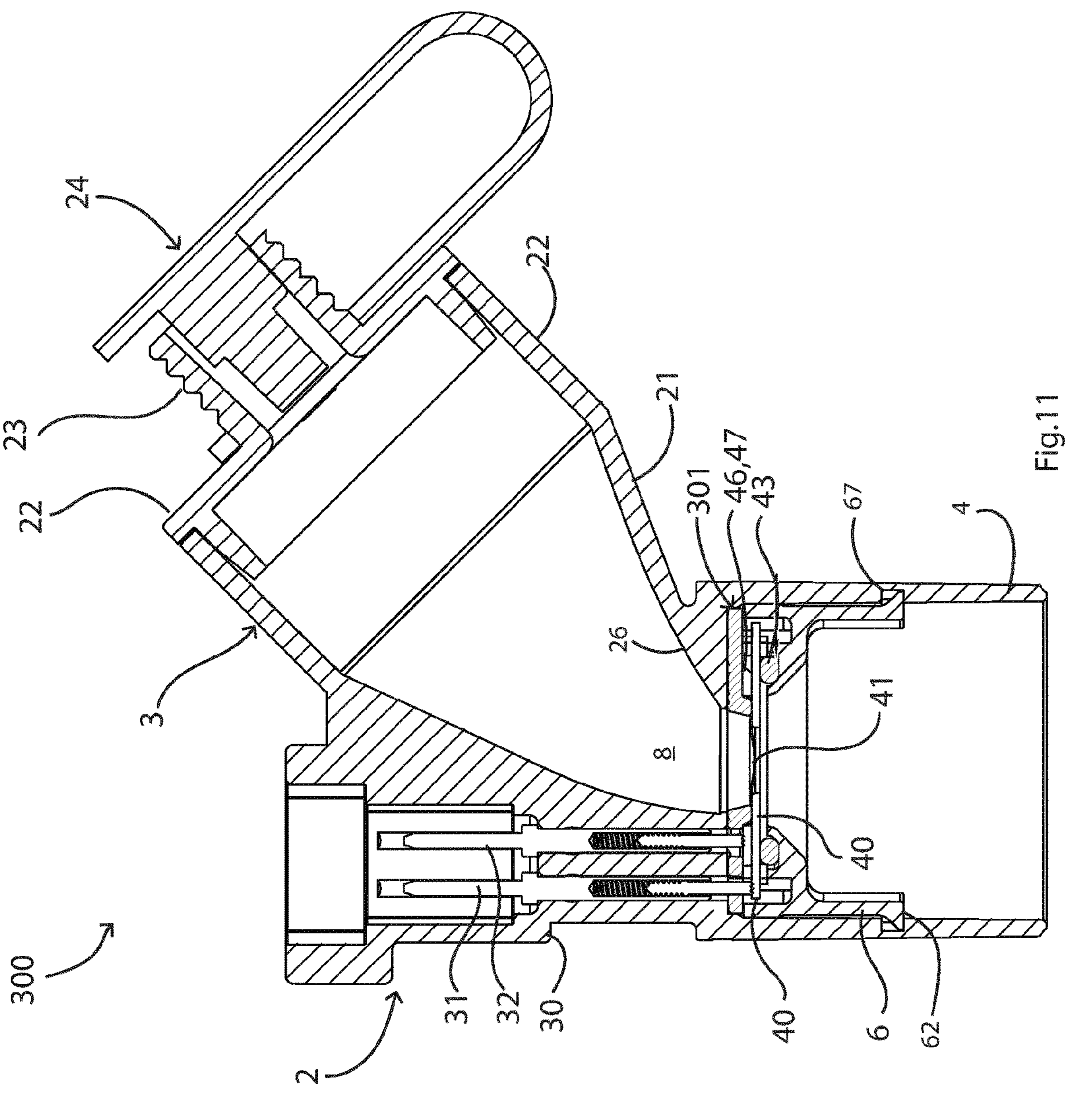
Figure 15:
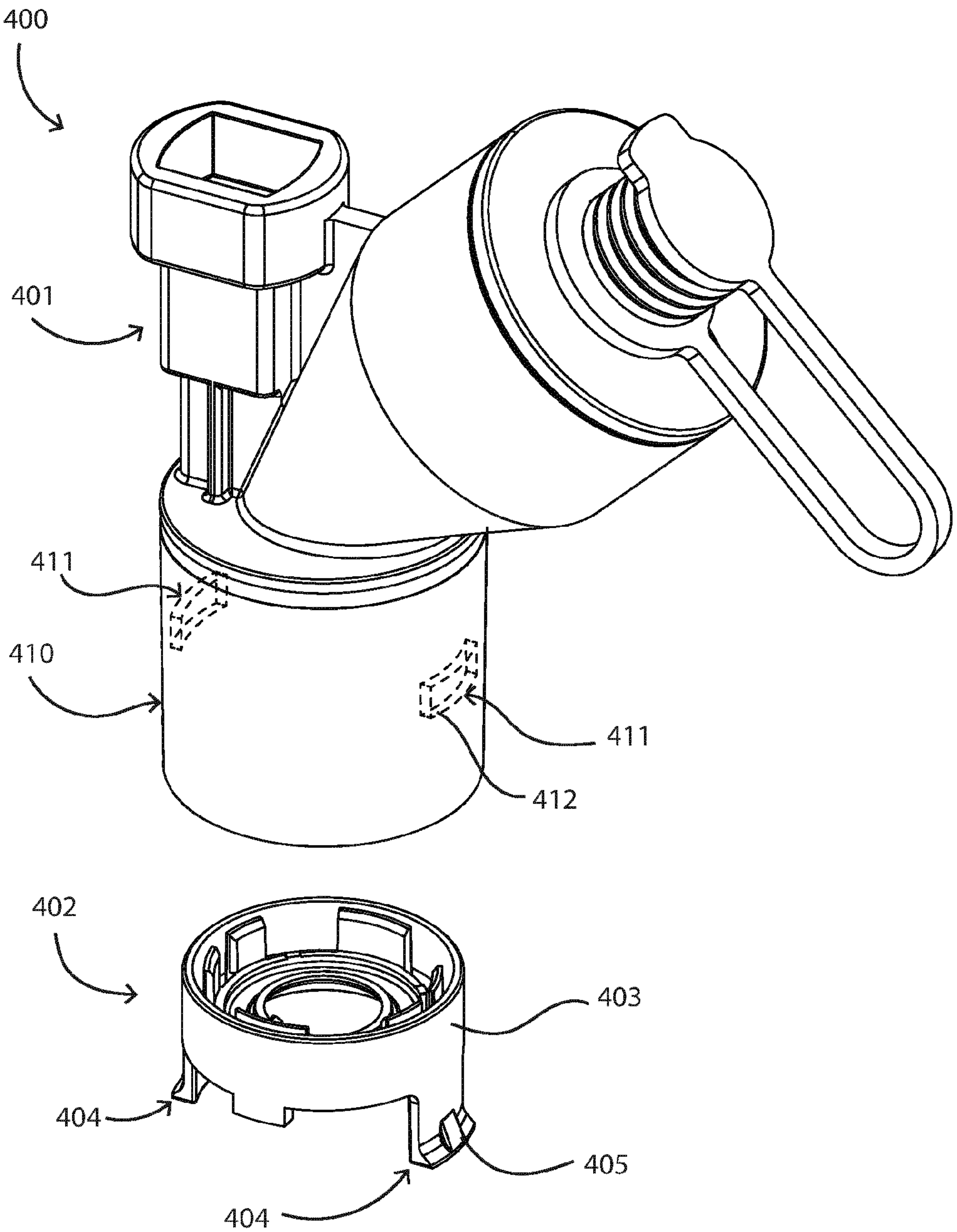
Figure 16:
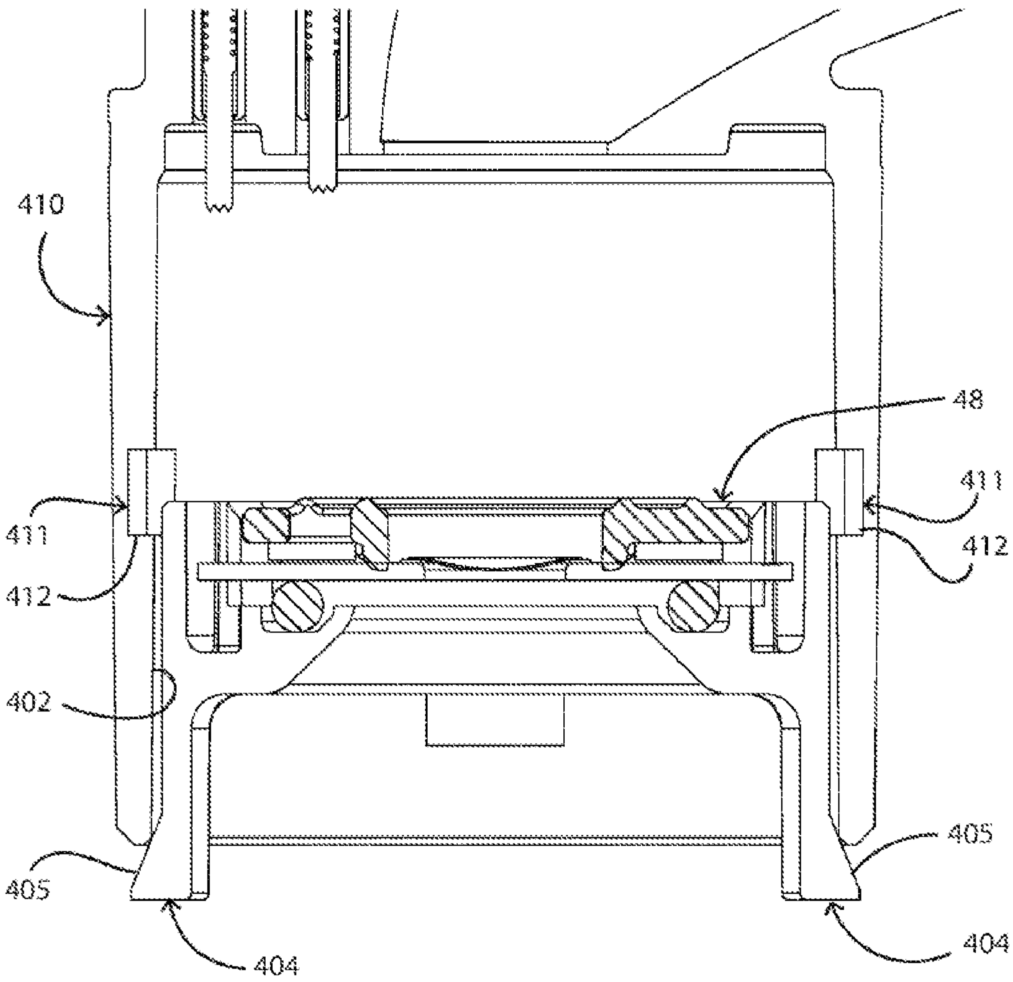
Figure 17:
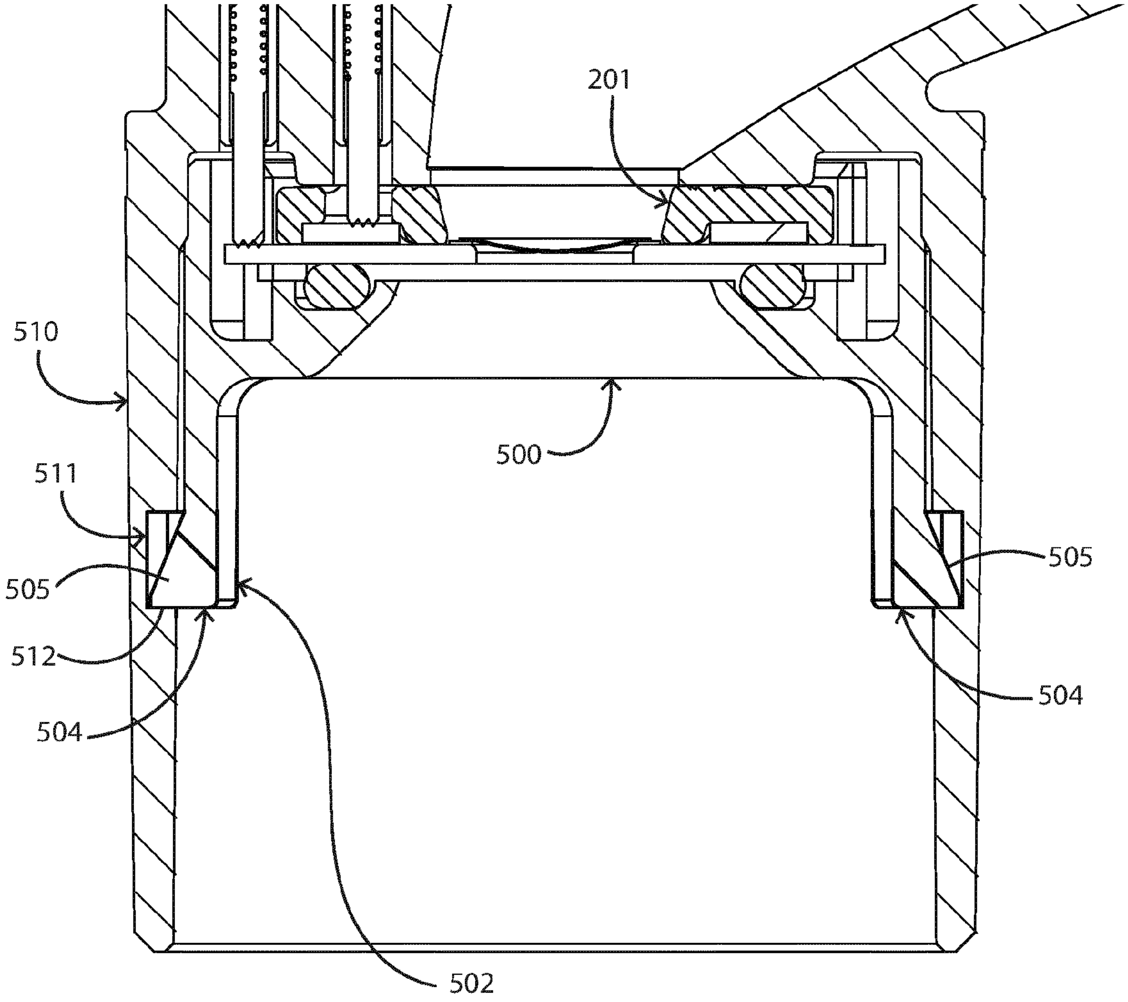
Figure 18:
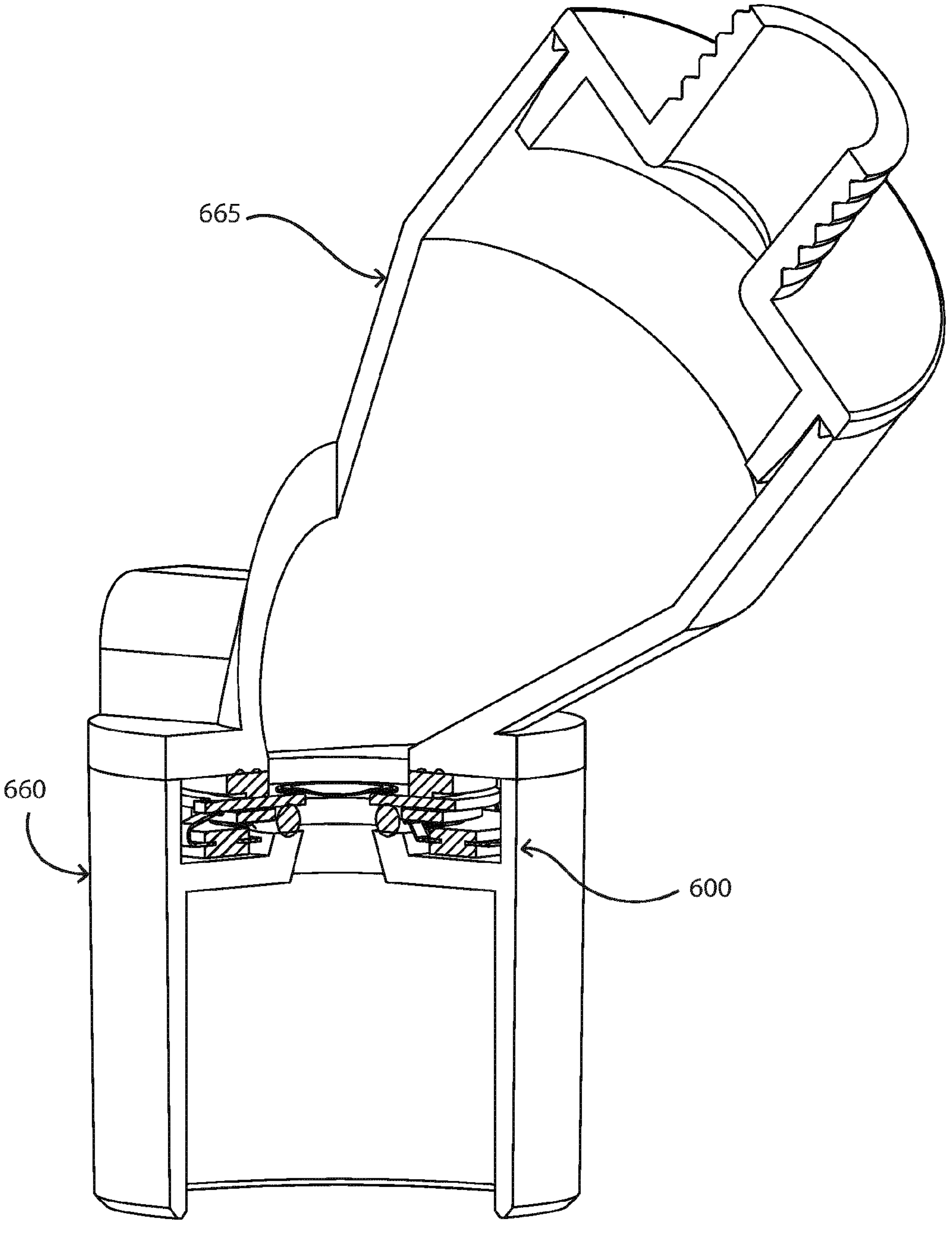
Figure 19:
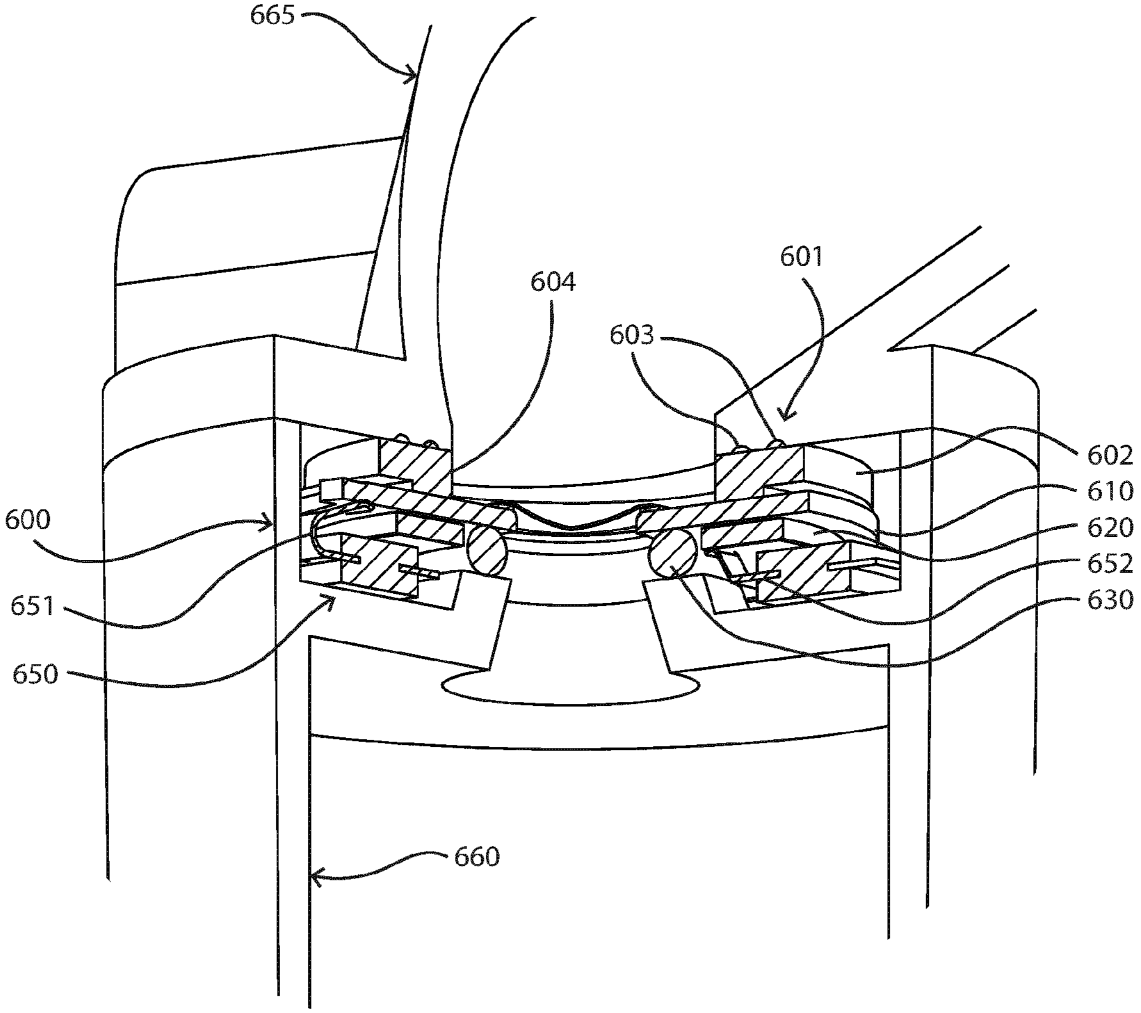

FIGS. 9 and 10 inclusive are views equivalent to FIGS. 5 and 6 of an alternative nebulizer, with a gasket having a downwardly-depending rim;

FIGS. 11 to 14 are views equivalent to FIGS. 2, 3, 5, and 6 of a further alternative nebulizer, in this case with a gasket having a body which extends further radially to encompass the radially outer conducting pin;

FIG. 15 is a perspective view of a nebulizer of an alternative embodiment, with the aerosol generator shown outside of the housing, and FIG. 16 is a diagrammatic cross-sectional view showing the aerosol generator being inserted to show function of ramps in retainer toes;

FIG. 17 is a diagrammatic cross-sectional view of an alternative nebulizer with ramp features of the FIG. 15 nebulizer, but in this case having a wider top (upstream) gasket;

FIG. 18 is a cut-away perspective view of a nebulizer with a gasket akin to that of earlier examples, but in this case power is conducted to the piezo element by spring clips rather than pins; and FIG. 19 is a cut-away perspective view showing the aerosol generator of FIG. 18 in more detail.

DESCRIPTION OF THE EMBODIMENTS

We describe aperture plate nebulizers which have a liquid vessel delivering liquid onto an aperture plate with apertures in the micro-metre size range, preferably directly by gravity, in which the vessel or reservoir is configured to provide a throat over the aperture plate (“AP”). The reservoir has features for reduction of bubble formation and consistent and predictable flow of liquid on the reservoir side of the AP. One such feature is a throat size which is too large for significant bubble formation. Preferably, the throat size has an area in the plane of the AP of at least 18 $mm^2$, more preferably at least 20 mm. more preferably at least 25 mm. more preferably at least 30 mm. In one example the throat area is about 34 $mm^2$, and is preferably in the range of in the range of about 32 $mm^2$ to 40 $mm^2$.

It is preferred that the throat area is at least twice the active area (the portion of the AP which vibrates, inside the attachment rim) of the aperture plate. In one example the AP is of electroformed metal with a diameter of 3.50 mm and an area of 9.6 $mm^2$. In this case the throat area is preferably at least 20 $mm^2$.

The aerosol generator may be of the type having a washer-shaped support to which is attached an annular piezoelectric vibration generating device on either the upstream or downstream side, and the aperture plate is connected by, for example, brazing to the internal rim of the support. The attachment of the AP to the support washer may alternatively be by adhesive, as described in our published patent specification WO2019/l 15221, the contents of which are incorporated by reference. In general, the AP has a rim which is attached to the support, and inside the rim there is the active portion, i.e. the portion which vibrates.

The aperture plate may have a main body (the vibratable, active, portion) with apertures of approximately 6 μm diameter and with a density of approximately 90 per mm in cross section (if the manufacturing uses photo-defined masking the density may be much higher, in the order of thousands per mm as described for example in WO2012/092163). Around this body there is the rim having a lower surface attached to the support washer. The AP is directly supported on the support washer laterally internally of the resilient seals and the vibratory drive piezo, without any mechanical clamping. There may be grooves in the surface of the AP rim, which assist adherence. The AP rim may be micro-machined in the lower surface to have multiple parallel anchor grooves each groove having a pair of side surfaces and a base surface, the base surface being substantially in the plane of the AP. The grooves are in the lower surface, extend generally in the radial direction, and have a zig-zag pattern as viewed in plan, with straight lengths between bends. In this example of adhesive attachment, in general, it is preferred to have as high a density of grooves as possible, consistent with maintaining sufficient mechanical strength in the aperture plate, especially at the rim where it is attached to the washer. For example, there may be 72 grooves in one example, and it is preferred that there are in the range of 30 to 130 grooves.

In general, it is preferred that, where there is adhesive attachment instead of brazing, anchor grooves are provided having a depth in the range of I0 μm to 40 μm, a width in the range of 20 m to 150 μm, an angular pitch in the range of 2.5° to 12.5°, and that they have at least one bend in direction, and each bend is at an angle in the range of 45° to 120°, and preferably in the range of 800 to 105°. Adhesive is applied to the rim on the underneath side between the rim and the washer. The washer is sloped away from the plane of the aperture plate with a convex curvature as viewed in cross-section. Advantageously, the adhesive forms a fillet where the washer bends away from the lower surface of the aperture plate. This provides excellent mechanical strength with integration of the washer to the aperture plate.

There is a gasket between the vessel housing and the aerosol generator at the AP support on the upstream side, the gasket having a rim extending between the support and the housing in the axial/longitudinal direction (parallel to the axis of the aperture plate), and a lateral portion extending radially to overlie at least some of the support. The configuration is such what when axial pressure is applied during manufacture the gasket tends to deflect radially outwardly, creating a tapered slope on the inside surface of the central opening in the gasket. This provides a funnel shape around at least some of the circumference of the throat. The housing configuration preferably provides a reservoir internal surface which forms a continuation of the gasket opening internal surface and the housing reservoir internal surface. Such a funnel shape may be provided by a top gasket which does not extend radially to a large extent, in some examples not extending as far as the piezo drive. In one such example it only extends radially to the extent of an inner rim which forms the gasket opening. This gasket internal liquid-contacting exposed surface is preferably not overhung by the housing and may be textured in a manner as described below for low propensity to bubble formation on the surface. Additionally or alternatively, there may be a hydrophilic coating on one or both of the gasket internal exposed surface and the reservoir surface.

By having different components in contact with the liquid, the gasket and the housing, it is convenient to provide a combination of surface types to optimise liquid flow to the AP, with minimization of bubble formation.

Preferably the gasket is supported together with the aerosol generator as a unitary assembly mounted on a retainer which engages as a unit with the remainder of the housing. This action is preferably movement towards the liquid supply chamber (reservoir) until a snap-fitting engagement of the retainer in place with the gasket axially compressed against the housing around the throat. The gasket is accurately and concentrically seated in an annular seat of the retainer, and this is preferably provided by resilient tabs which are arc-shaped and spaced-apart around the circumference of the gasket seat.

Figure 1:
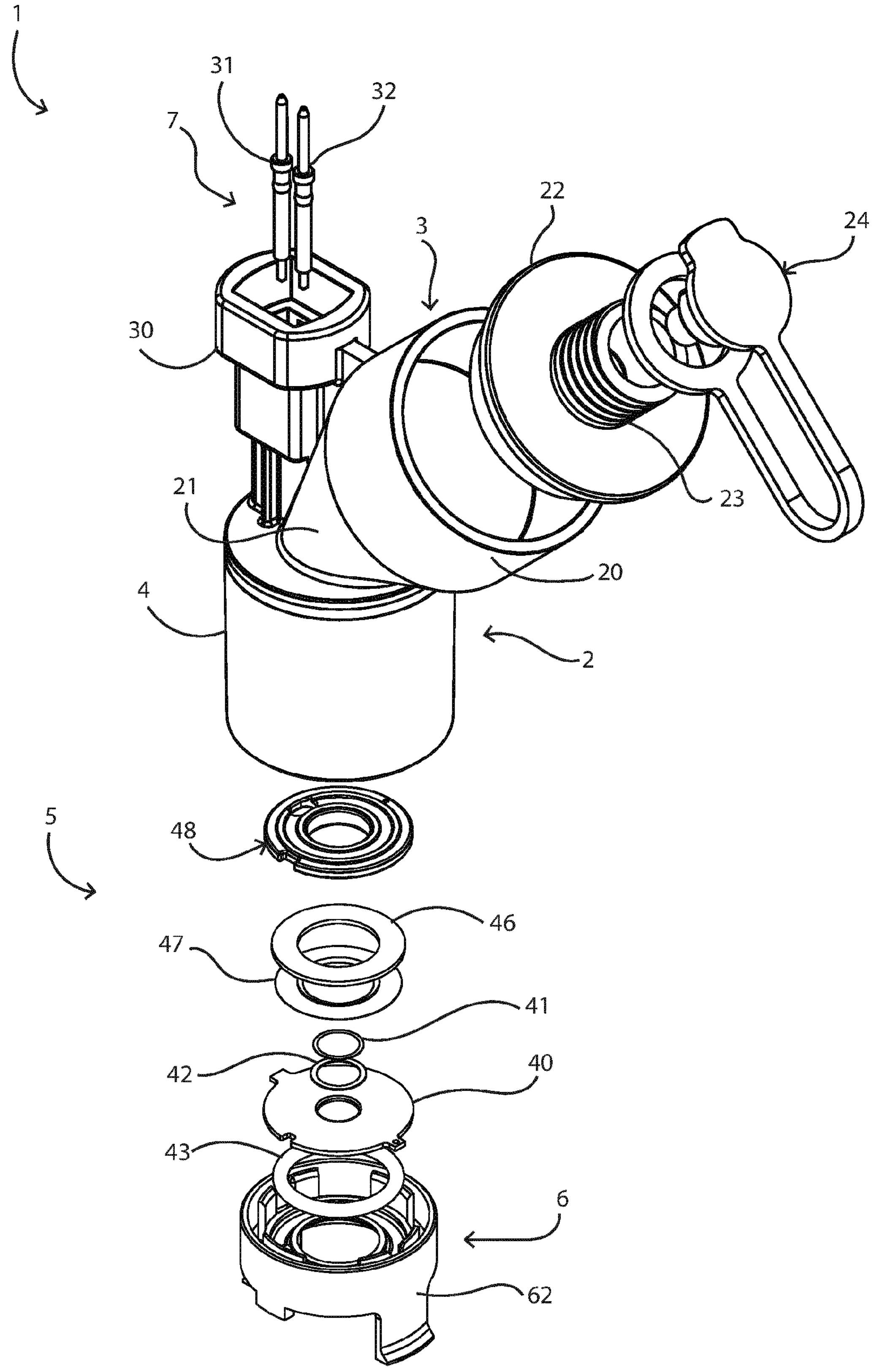
FIG. 1 is a perspective exploded view of a nebulizer.

Referring to FIG. 1 the following main components of a nebulizer 1 are illustrated:

2, integral plastics housing body,
3, liquid supply chamber (or "reservoir"),
4, aerosol delivery tubular outlet,
5, aerosol generator assembly,
6, retainer, supporting the aerosol generator 5 in the integral housing body 2;
20, reservoir tubular top part,
21, reservoir funnel-shaped lower part ("funnel"),
22, liquid supply chamber cap;
23, cap tubular opening,
24, cap silicone plug,
30, power conducting pin support part of the housing body 2;
31, 32 conducting pins extending through the pin support housing part 30;

The reservoir top part 20 is in fluid communication with the inclined funnel-shaped lower part ("funnel") 21 for delivering liquid onto the aperture plate ("AP"). The aerosol delivery tubular outlet 4 is below the AP, is integral with the reservoir parts, and is co-axial with the AP. The axis of the funnel 21 is inclined to the AP axis. This allows use of the nebulizer at a wide range of orientations with gravity fall of the liquid onto the AP.

The conducting pins 31 and 32 are for conducting power to a piezoelectric vibration generator of the aerosol generator, and are retained within, and guided by, the pin housing part 30 of the housing body 2.

The retainer 6 is for carrying the aerosol generator assembly 5, pressed against a lower surface of the funnel 21. The aerosol generator assembly 5 comprises, from top down, an upstream seal namely a gasket 48, a piezoelectric vibration generator ("piezo") 46, an adhesive ring 47 under the piezo 46, an aperture plate 41, a braze ring 42, an annular washer-shaped aerosol generator support ("washer") 40, and a downstream O-ring 43. This assembly is supported by the retainer 6 and is surrounded by the aerosol delivery tube 4. The piezo adhesive ring 47, while shown for illustrative purposes as a discrete item is in fact bonded between the piezo 46 and the washer 40, attaching the piezo to the washer in a manner which conducts electrical power to the underside of the piezo 46. Likewise, the braze ring 42 is an integral part of the rim of the aperture plate ("AP") 41 and the internal rim of the washer 40, attaching the AP to the washer. In other examples the attachment of the AP may be bonded rather than brazed. This example involves an electroformed aperture plate 41 with "hourglass" shaped apertures. However, in other examples the aperture plate may be formed by photo-defined technology as described in our prior patent specification nos. WO2012/092163 or WO2013/186031. There may be a reservoir layer of liquid supply cavities over the aerosol-forming apertures, formed in a manner for example as described in WO2012/092163 or WO2013/18603 1, and these may have a diameter in the range of 20 m to 400 μm.

The aperture plate 41 apertures have an outlet opening diameter in the range of 1 m to 10 μm, and in one example about 2 μm to 3 μm.

Figure 2:
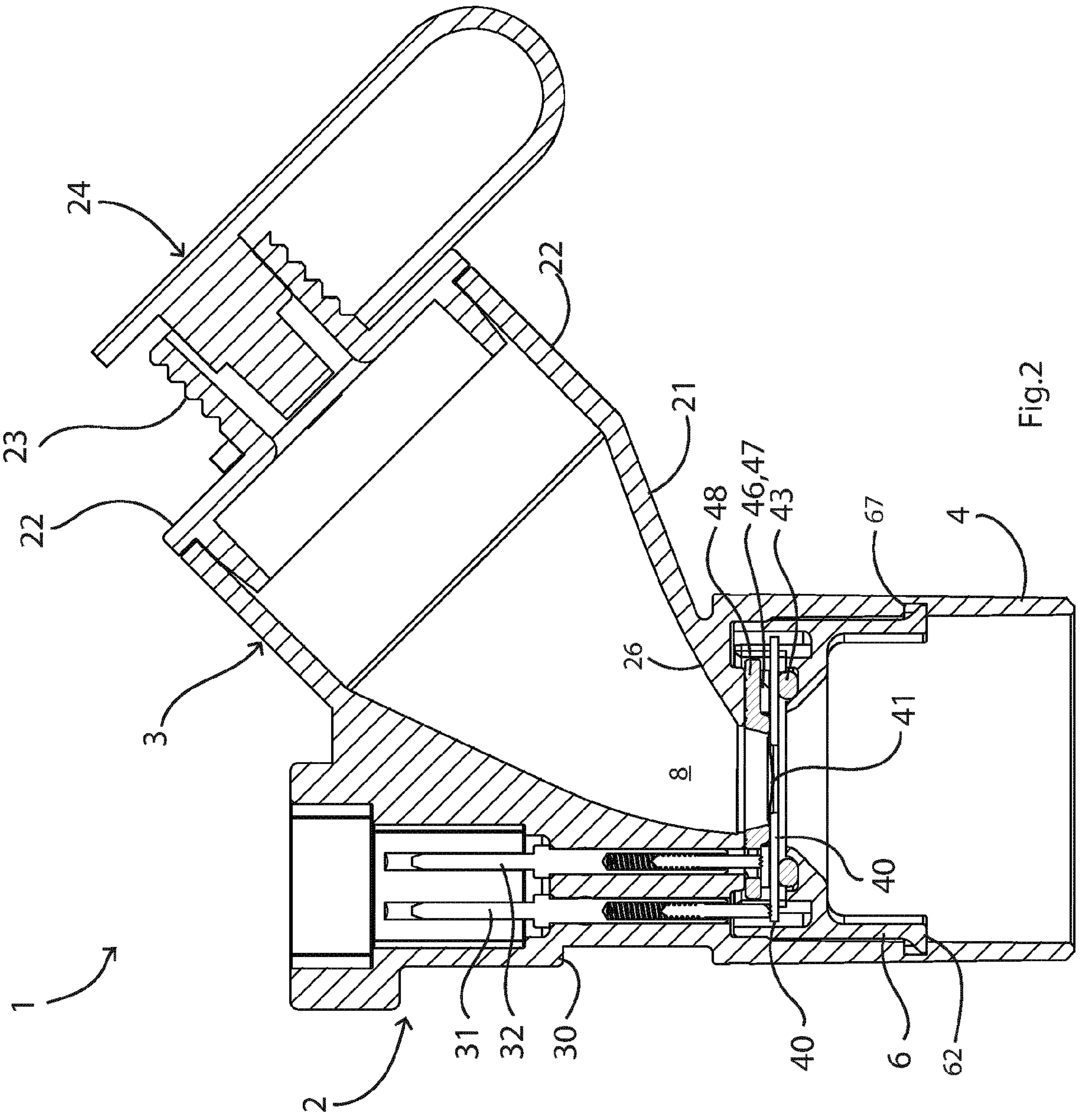
FIG. 2 is a sectional elevational view of the nebulizer.
Figure 3:
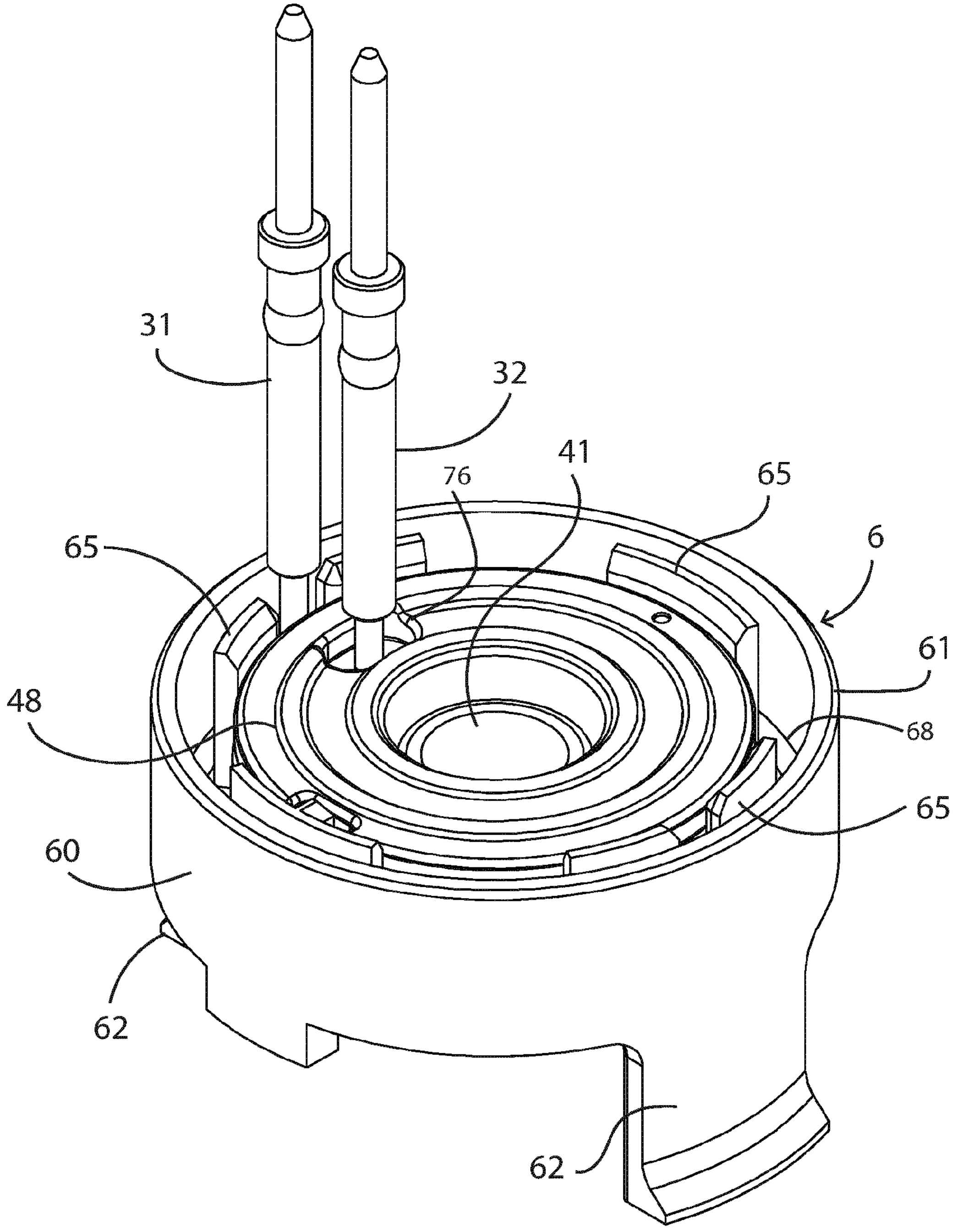
FIG. 3 is a perspective view of the aerosol generator when removed from the housing.
Figure 4A:
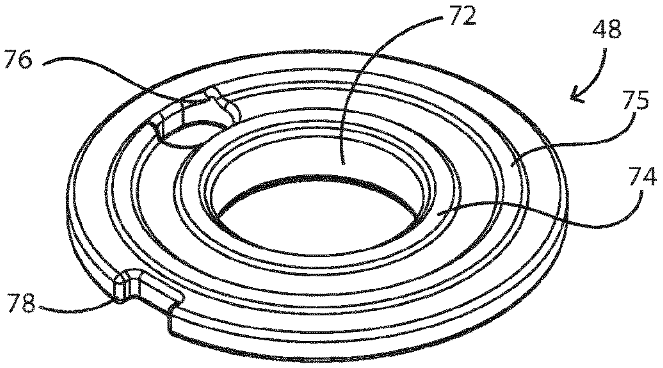
FIG. 4 is a set of views of atop gasket of the aerosol generator.
Figure 4B:
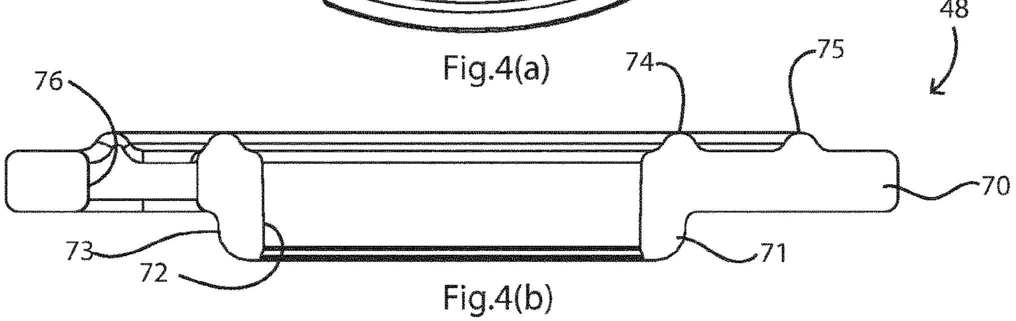
Figure 4C:
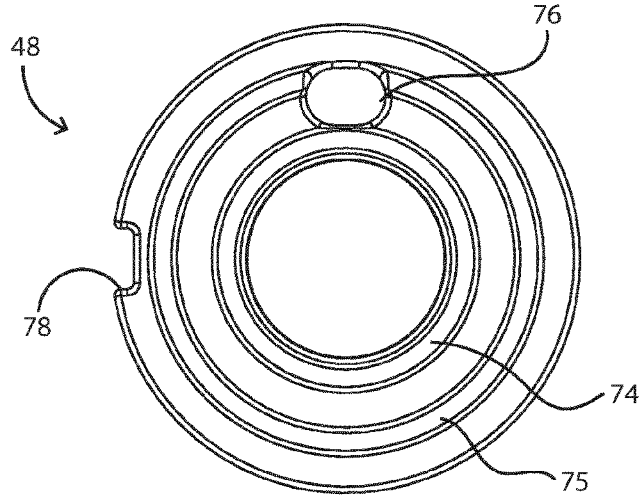
Figure 4D:
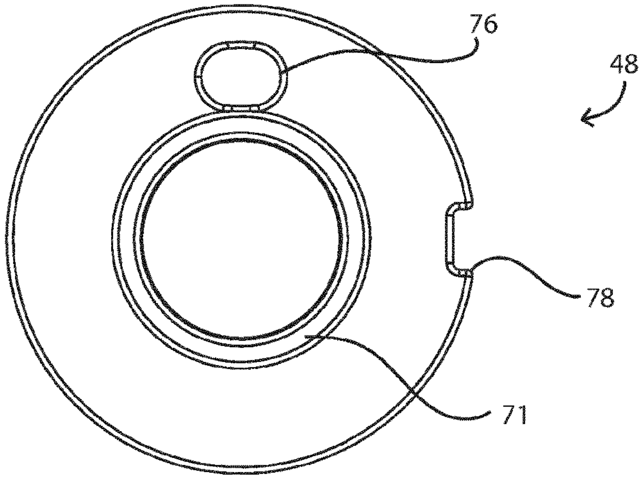

Referring also to FIGS. 2 and 3, the retainer 6 is configured so as to securely support and contain the components of the aerosol generator assembly 5. It has a circumferential wall 60 with a top rim 61 and a pair of lower depending legs 62 with toes which snap fit as clips into corresponding elongate tabs 65 define the outer surface of a circular seat for the gasket 48, and FIG. 3 shows the gasket 48 retained within the tabs 65 in a concentric position.

The retainer 60 also forms an annular seat 68 for the downstream O-ring 43, shown most clearly in FIGS. 5 and 6. The washer 40 is supported underneath by the O-ring 43 housed within the groove 68 of the retainer 6, the washer 40 resting on the O-ring 43 and itself supporting the piezo 46 adhered to the washer 40 top surface. The AP 41 is attached by the braze ring 42 to the washer 40.

The liquid supply reservoir funnel 21 has an internal tapered surface 26 inclined inwardly towards the AP 41, defining a throat 8 over the AP together with the gasket inner surface 72. The latter is not overhung by the housing, forming a continuation of the housing surface. By having two components, the gasket and the housing forming a reservoir shape leading to the aperture plate, it is convenient and versatile to provide a combination of surface types to optimise liquid flow to the AP, with minimization of bubble formation.

The housing 21 forms a continuation of the gasket 48 inner surface 72, so that they together provide a liquid flow funnel towards the AP. As described in more detail below, this allows not only smooth and streamlined flow, but also allows the provision of a different surface near the AP, by for example a desired roughness of the gasket surface 72 for optimisation of flow characteristics and/or and bubble prevention. The reservoir 3 is tilted away from the axis of the AP, and forms a much greater angle to the AP axis on the lower side. On the lower side, the funnel wall 26 diverges away from the throat area at an angle to axial preferably greater than 45° and more preferably greater than 50° and still more preferably greater than 55° for at least some of the circumference of the throat. In this particular example the angle is about 60° at its greatest. This provides a maximum amount of space over the AP, thereby minimising surface area for bubble growth, as described in more detail below.

The compressed axial (aperture plate central longitudinal axis) dimension distance between the plane of the rim of the aperture plate and the bend in the housing where it is splayed out is 2.3 mm, and is more generally preferably in the range of 1.8 mm and 3.0 mm. This provides splaying out a short enough distance from the AP to help minimise bubble prevention. The fact that about 1.8 mm of this dimension is provided by the gasket inner surface is helpful, as it may have a desired surface roughness to additionally prevent bubble formation. In general, it is preferred that the axial dimension of the gasket at the throat is in the range of 1.5 mm to 3.0 mm.

The top (upstream) gasket 48 is sandwiched between and compressed by the washer 40 and the bottom surface of the housing body funnel 21. The gasket 48 counterbalances the force from the O-ring 43 and from the pins 31 and 32.

As shown particularly in FIG. 4 the gasket 48 comprises a body 70 of material moulded to form a downstream-depending circular rim 71 with the internal surface 72 forming an opening, which is part of the throat 8, for liquid supply to the AP. The rim 71 provides a gasket depth which is greater than the depth of the remainder of the body 70, and because it forms part of the opening surface 72, it extends this opening surface in the downstream direction. In this example the depth of the rim 71 below the body 70 is 0.8 mm, and in general it is preferred that it is in the range of 0.5 mm to 1.1 mm. The body extends in the radial (lateral) direction to provide a washer annular shape in general outline, and so it thereby interfaces between a number of components, such as between the piezo 46 and the reservoir 21, and between the support 40 and the housing 21. It therefore provides sealing and balance within the aerosol generating core.

The gasket body 70 is also an integral base for inner and outer concentric circular top ridges 74 and 75 extending in the upstream direction for contact with the housing reservoir. These have a height of 0.3 mm and in general it is preferred that they have a height in the range of 0.1 mm to 0.5 mm. There is a through hole 76 in the body 70 to receive the radially inner conducting pin 32. There is also a slot 78 in the outer edge of the body 70 for mistake-proofing the assembly. It prevents the seal being loaded into the retainer if it is not in the correct annular orientation.

The gasket 48 is of medical grade liquid silicone rubber supplied as two component compounds which are mixed together and injected into a hot mould to cure. In general, it is preferred that the gasket has a Shore hardness in the range of 20-80 Shore A, more preferably in the range of 30 to 60 Shore A The dimensions of the gasket 48 are in this case, when relaxed:

internal diameter, 6.2 mm;

external diameter, 14.7 mm;

maximum depth, 2.1 mm;

height of ridges 74 and 75, 0.3 mm;

height of ridge 71 with respect to the body 70, 0.6 mm.

In this example the throat 8 is about 6.0 mm diameter, as defined by the opening 72 of the gasket 48 at its lower end closest to the AP. This large diameter throat reduces risk of bubble entrapment due to air ingestion.

The gasket 48 is tolerant to dimensional variation of plastics housing components from the point of view of sealing, protecting the piezo 46 and the electrical connections.

The gasket 48 is located on the retainer 6 during automated assembly, as shown in FIG. 3. This allows accurate placement and automated manufacturing, which is particularly important for accurate location of the gasket relative to the aerosol generator 5 components.

Referring again to FIGS. 5 and 6, the positions before and after full insertion of the retainer 6 are shown, in which the retainer 6 and the aerosol generator 5 are provided as a sub-assembly, and are pushed upwardly against the funnel 21 lower surface. As is clear from FIG. 6, in the final position the legs 62 are snap-fitted into the notches 67 of the aerosol outlet tube 5, at which position the downstream O-ring 43 and the gasket 48 are slightly compressed axially. Hence, the manufacturing process can be efficient and tolerant of small placement variations. It is simple to axially load the components of the aerosol generator 5 (as best shown aligned for manufacture in FIG. 1), and to then press them axially upwardly against the housing wall 21 lower surface. This is a robust method of seal location. FIGS. 5 and 6 also show a diverging surface 69 downstream of the throat 8, for aerosol flow from the AP.

The throat 8 diameter of about 6.2 mm is achieved through the opening 72 diameter of the gasket 48. As shown in FIG. 6, there is a tapering of the opening due to the axial compression, providing a funnel shape. The diameter narrows and at the downstream extremity may be in the range of 0.1 mm to 0.3 mm less than the nominal 6.2 mm diameter when the gasket is relaxed.

The tapering of the opening is contributed to by the rim 71 protruding downwardly and being much more deformable than the body 70.

Physical Support and Sealing Benefits for the Aerosol Generator 5

The aerosol generator 5 is under vertical compression across a large area, providing an excellent seal which is more tolerant to dimensional variation of the plastics housing components.

The upper ridges 74 and 75 compress with the axial compression as shown in FIG. 6, providing grip and robust stability in the high frequency environment, in which the plate may be vibrating at for example 128 kHz. Moreover, the gasket 48 covers the piezo 46, thereby limiting the potential for ingress of moisture from the funnel 21 at the throat 8 area to the electrically-conductive components 31, 32, 46, and 40.

Referring again to FIG. 6, it will be clear from this diagram that the gasket 48 provides a large degree of counterbalancing of forces which arise from pressing by the conducting pins 31 and 32 against the piezo 46 and the washer 40. This is contributed to by the large bulk of the gasket's body 70 and large surface abutting the underside of the funnel 21. Moreover, the gasket 48 acts as a cover over the piezo 46, thereby helping to protect it from ingress of moisture in the highly humid and high-frequency environment.

The pair of upper ridges 74 and 75 are particularly beneficial because they ensure uniform contact with the funnel 21 all around the gasket's periphery, but are not so high that they prevent contact by the remainder of the upper surface of the gasket when under axial compression.

Bubble Prevention

The gasket 48 has in this example a fine textured surface finish with arithmetic roughness average, Ra, in the range of 1.6 m to 3.2 m. The roughness average parameter Ra is defined in ISO4287:1998+Al:2009 at 4.2.1. Ra is calculated by measuring the average length between the peaks and valleys and the deviation from the mean line on the entire surface within the sampling length. Ra averages all peaks and valleys of the roughness profile and then neutralizes outlier points so that they have no significant impact on the final results. The Ra range of 1.6 μm to 3.2 μm is equivalent to 24 to 30 on the VDI 3400 (Charmilles) surface roughness scale ("VDI").

Referring to FIG. 8 the surfaces of two gaskets are shown with a magnification of 1000. The gasket on the left has a surface finish roughness of average of about 1.8 μm, and the gasket on the right-hand side has a surface finish with a roughness average of about 2 μm to about 3 μm. The surface roughness is more visible in the surfaces facing the camera as they are in focus. It is possible to be more accurate about roughness of the left-hand gasket because it is moulded, and surface roughness of the mould steel is accurately known.

Such a surface roughness helps to prevent small bubbles from adhering for a significant time to the scale of magnitude of the roughness is comparable to that of the bubbles which tend to congregate and coalesce above the rim of the AP (aperture size 2 μm to 6 μm, and vibration frequency of about 128 kHz. A surface roughness Ra value of 1.6 μm to 3.2 μm is particularly effective for an aperture plate aperture diameter in the range of about 1 μm to 6 μm, and/or a vibration frequency in the range of about 60 kHz to 200 kHz, more preferably in the range of 100 kHz to 1 60 kHz.

FIG. 7 shows bubbles which naturally develop on the upper surface of the AP, especially around its rim, due to air being drawn up thorough the apertures due to the AP vibration at a frequency of 128 kHz. We have found that a surface roughness value of Ra in the range of about 1.6 μm to 3.2 μm is better than a smoother surface. Bubbles rising from the AP tend to be less likely to stagnate on the surface of the gasket.

The desired surface roughness may be achieved in any desired manner. The image on the left of FIG. 8 is of a gasket formed by injection moulding, and on the right by 3D printing.

The gasket may for example be moulded from a thermoplastics elastomer material such as those grades supplied by BASF, or as mentioned above by additive manufacturing technologies (3D printing).

There is excellent liquid flow to the AP due to the reservoir having an internal smooth funnel surface leading into a softer material with a higher surface roughness.

In other embodiments the gasket and/or the funnel are coated with a hydrophilic coating, to further reduce risk of bubble stagnation and coalescence. The hydrophilic coating would be thin enough not to affect the surface roughness, but would deter bubbles from coalescing. The hydrophilic coating preferably has a thickness in the range of 0.5 μm to 2.0 μm.

In various examples the hydrophilic coating may be of a monomer composition with vinyl acetate, hexamethyldisiloxane (HMDSO) mixed with oxygen in a given ratio with more HMDSO than 02.

Alternative Gasket Configurations

Referring to FIGS. 9 and 10 a nebulizer 200 has a gasket 201 instead of the gasket 48, and all other components are the same and are indicated by the same reference numerals. The gasket 201 has a pins 31 and 32. This has the benefit of increasing the extent of enclosure around the piezo, and of contact with the vibrating surfaces, both the washer and the funnel 21. The enveloping on both radial sides and the top side of the piezo helps to ensure reliability even if there is a slight leak of moisture into the space over the washer due to a gap evolving between the retainer and the housing.

Figure 12:
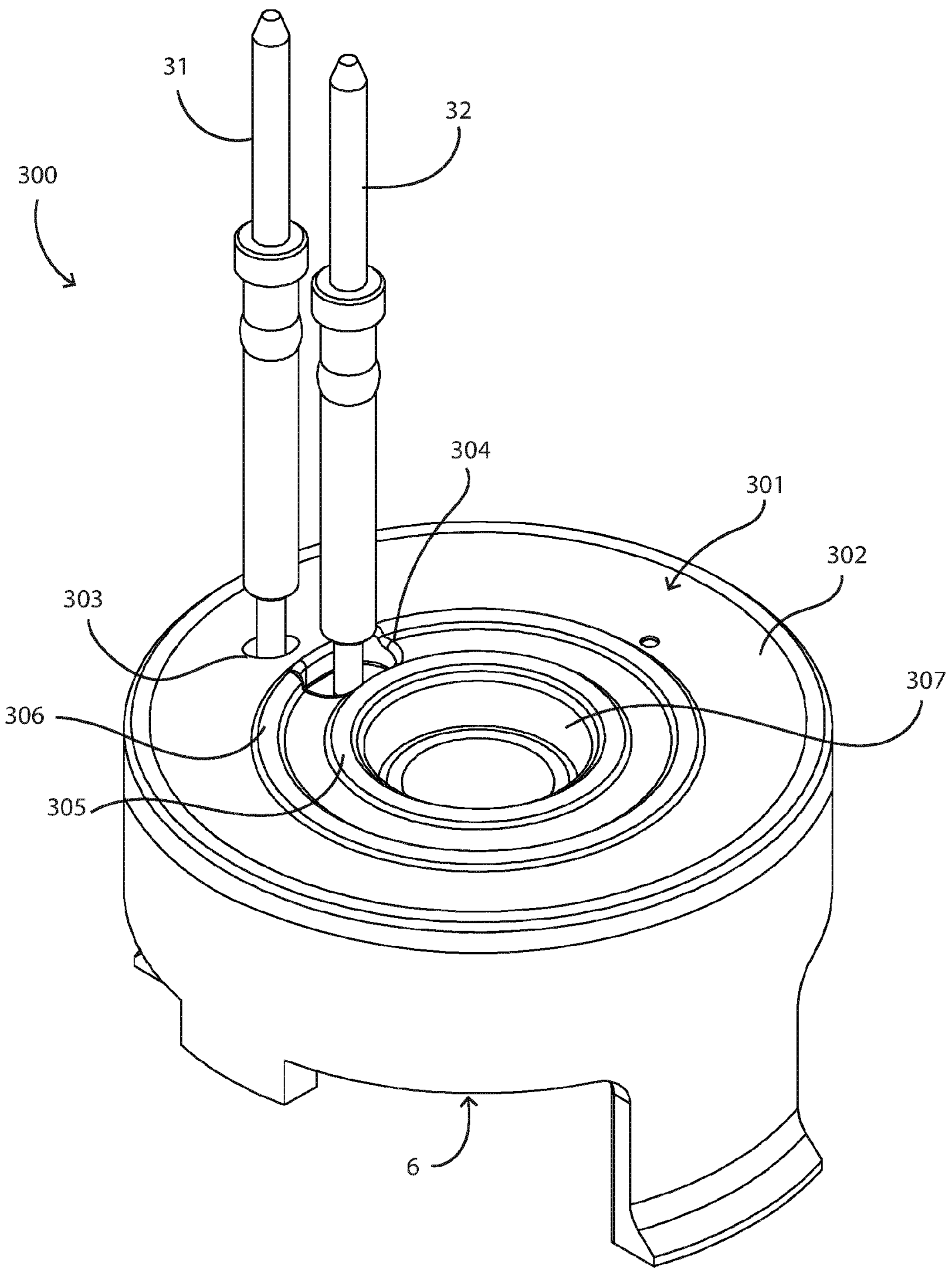
Figure 13:
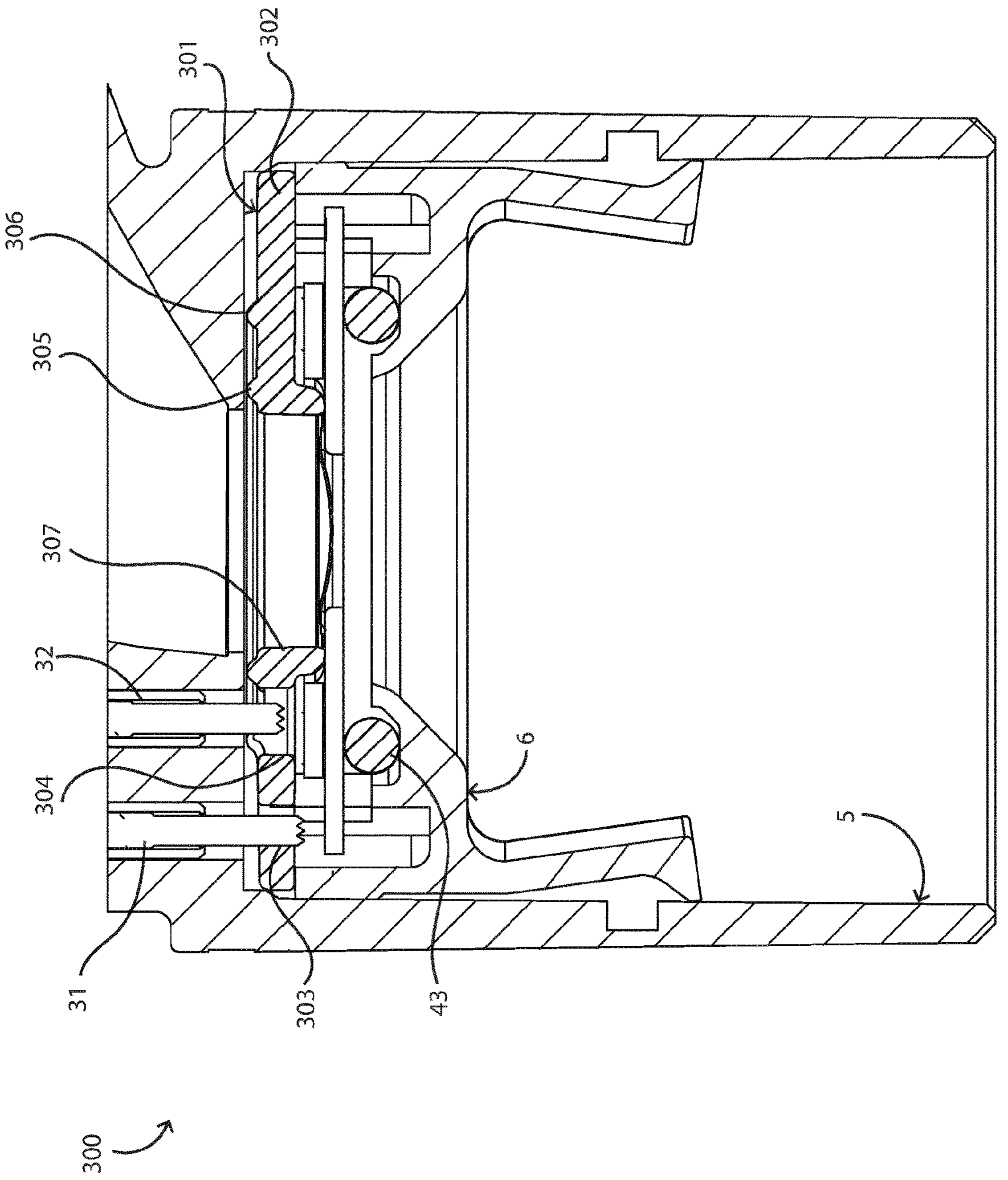
Figure 14:
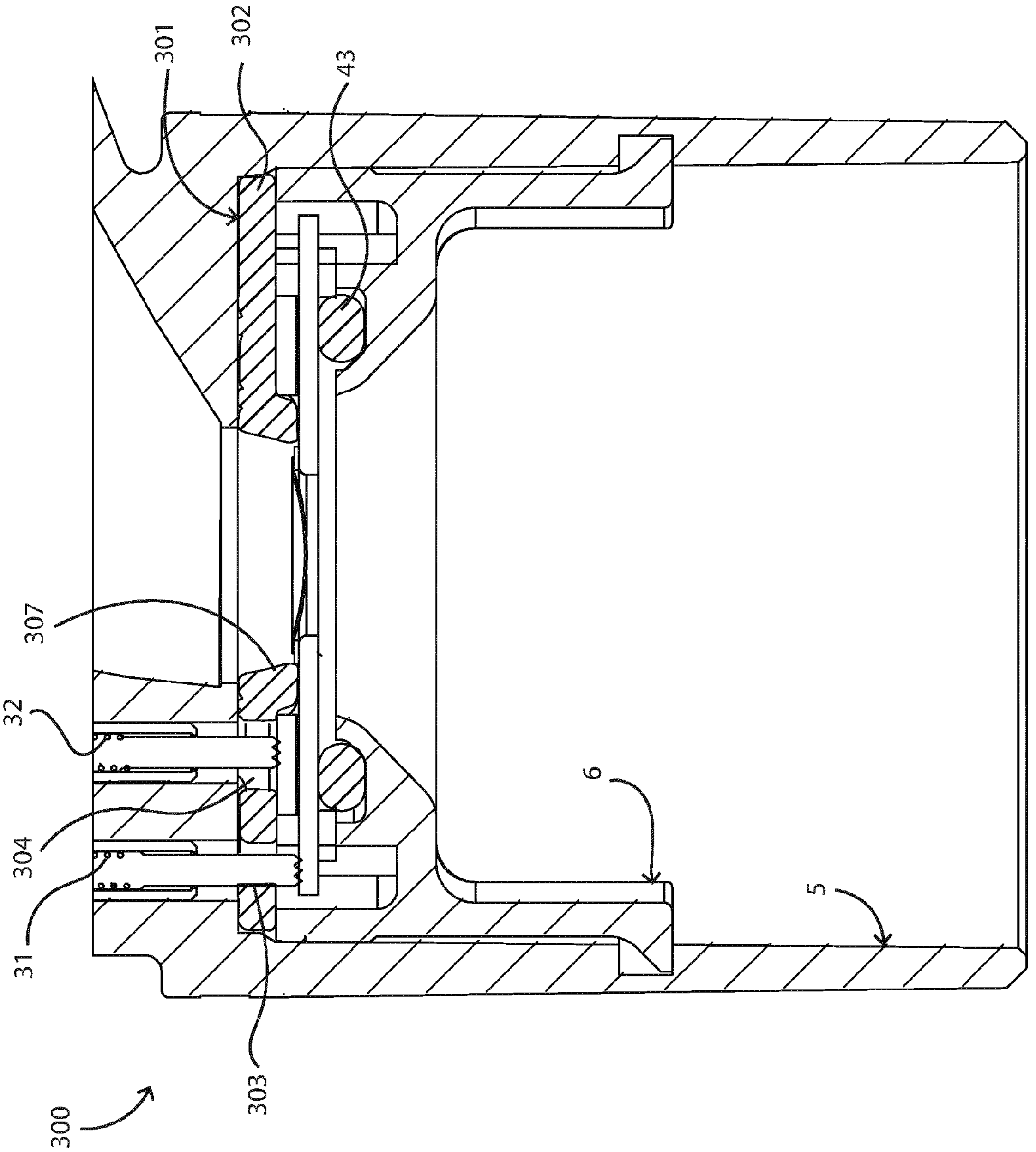

Referring to FIGS. 11 to 14 an alternative nebulizer, 300, has a gasket 301 instead of the gasket 48, and again the other components are the same and indicated by the same reference numerals. The gasket 301 has a body 302 extending further radially, and has an aperture 303 for the radially outer pin 31 in addition to an aperture 304 for the pin 32. There are upstream ridges 305 and 306 which are similar to the ridges 74 and 75 of the gasket 48. The gasket body 302 extends radially sufficiently far to engage at its peripheral edge the housing 5. The gasket 301 has an opening surface 307 which forms part of the throat over the AP, as best shown in FIGS. 12 and 14.

This arrangement has the benefit of providing greater surface contact area on the top. Also, it provides a resilient seal between the two mating plastics parts, the retainer and the reservoir/housing.

Alternative Retainer

Referring to FIGS. 15 and 16 an alternative nebulizer 400 has a housing 401 with an aerosol outlet conduit 410 with a pair of opposed recesses 411 with lower edges 412. The retainer 402 has a tubular body 403 with a pair of opposed legs 404 with toes for snap-fitting in the opposed recesses 411, as for the other embodiments. However, in this case each leg 404 additionally has a ramp 405 facing radially outwardly, thereby assisting insertion of the retainer 402 during manufacture. This reduces the impact when the body is placed down over the retainer during assembly.

FIG. 17 shows a retainer 500 having a main body 502 with opposed legs 504 with toes having ramps 505. These snap-fit into recesses 511 with lower edges 512. In this case the gasket is the gasket 201, which extends fully radially over the piezo and as far as the housing and engages the support radially outwardly of the piezo.

The manner of providing power to the piezo element may be different from that illustrated, without pins which engage the piezo element and support. For example, as shown in FIGS. 18 and 19 a nebulizer has a top housing 665 providing the funnel and a lower aerosol outlet part 660 which supports an aerosol generator assembly 600. In this case there is a top gasket 601 which forms part 620 is adhered by conductive adhesive to the underneath (downstream) side of the support 610, hence removing a component from above the support and leaving more scope for a wider throat area. The washer 610 is supported underneath by an O-ring 630, in a manner broadly similar to that of the other embodiments. However, in this case power is provided by an annular spring clip assembly 650 having an annular body supporting a C-shaped clip which extends radially outwardly and back inwardly to engage the underside of the washer 610. There is also a clip 652 in the general form of a leaf spring which engages the underside of the piezo element 620. Hence power to the top surface of the piezo element 620 is provided via the washer 610 by the spring clip terminal 651, and directly to the bottom surface of the piezo element by the spring terminal 652.

It will be appreciated that the invention provides a nebulizer with many significant improvements arising form the upstream resilient seal. By this seal forming part of the throat in the reservoir and also acting as a seal it is a single part which performs two very important functions. It is particularly advantageous that there is no overhang by the housing over the exposed surface of the upstream resilient seal, providing a streamlined approach for liquid delivery to the aperture plate. Moreover, it is possible to modify the seal exposed surface to provide an enhanced benefit for bubble prevention, such as a roughened surface. It is particularly advantages in the examples of the seal exposed surface being funnel-shaped. Another major advantage is that the arrangement of the housing and the upstream seal allows a relatively wide throat, thereby contributing to predictable and efficient liquid flow to the aperture plate.

The invention is not limited to the embodiments described but may be varied in construction and detail. For example, the throat area may have an area greater than 34 mm 2. It is envisaged that in other examples the gasket may have a downwardly-depending rim akin to that of the gasket 201 and a top surface area and radial extent akin to that of the gasket 301. The downstream resilient seal may not be in the form of an O-ring. It may be a ridge of resilient material extending from the housing, and it may be affixed to the housing. It may have some features of the gasket, such as a body which extends radially outwardly to an extent greater than the O-ring as illustrated. It is also envisaged that in other examples the top gasket downstream-extending rim is not necessarily at the gasket opening, but could be radially outward from it by a small extent.

Also, as shown in FIGS. 18 and 19 power may be supplied by contacts other than conducting pins. The power conductor may comprise at least one first spring contact engaging the support or vibration generator, and a second spring contact engaging the other of the vibration generator or delivery to the vibration generator. The support may extend further radially than the vibration generator, and the first spring contact engages a support surface laterally of the vibration generator. The second spring contact may directly contact the vibration generator. At least one of said spring contacts may be in the form of a resilient ridge which is arc-shaped in axial (longitudinal) view, and the terminal 652 is an example. The resilient ridge may extend at least partly around the aperture plate. The resilient ridge may extend in the upstream direction from a contact assembly base, and the base may also support a spring contact which extends radially outwardly and bends radially inwardly to engage a support or vibration generator surface. The bend may provide the resilience for the spring contact. A spring contact with a bend may engage the support radially outwardly of the vibration generator.

The spring contacts may be mounted to a contact assembly which is mounted to the housing on either upstream or downstream sides, but preferably downstream as this allows more space for a wide throat area.

It is also envisaged that the gasket may only have a very limited body extending radially, but provides excellent advantages by way of resilient upstream support and also preferably roughness of the surface in contact with the liquid where it forms part of the funnel throat. In one example the gasket body only extends to approximately the radial extent of the ridge 74. In general, any of the features of nebulizers described herein may be employed in different combinations with other features than illustrated. Also, it is envisaged that the housing may be provided by a greater or lesser number of parts which interconnect together. For example, the aerosol outlet may be a discrete component which fits to the reservoir or to an intermediate housing component. Ultrasonic welds may for example be used to join parts together.

The invention claimed is:

1. A nebulizer comprising:

an upstream housing element forming a power conductor support part, a tubular outlet, and a reservoir upstream of the tubular outlet, the reservoir including a tubular top part, a funnel-shaped lower part, and an internal surface forming a throat over a vibratable aperture plate;

a reservoir cap upstream of the reservoir of the upstream housing element;

a downstream housing element configured to engage with the upstream housing element;

a power conductor assembly at least partially disposed within the power conductor support part of the upstream housing element and configured to convey power to an annular vibration generating element for vibrating the vibratable aperture plate; and an aerosol generator assembly disposed between the upstream housing element and the downstream housing element, the aerosol generator assembly comprising:

an annular member;

the vibratable aperture plate, the vibratable aperture plate including a plurality of apertures;

the annular vibration generating element;

a first sealing member upstream of the vibratable aperture plate and axially compressed between the throat and the annular member, the first sealing member including a ring shape and an opening having an internal surface forming an extension of the throat; and a second sealing member downstream of the vibratable aperture plate, wherein, in a cross section of the first sealing member, the internal surface of the opening of the first sealing member is substantially flat and extends substantially from the throat of the upstream housing element to the annular member.

2. The nebulizer of claim 1, wherein the first sealing member is axially compressed between 1) a lower extremity of a wall defining the internal surface forming the throat of the upstream housing element and 2) the annular member.

3. The nebulizer of claim 1, wherein a diameter of the opening of the first sealing member is greater than 5 mm.

4. The nebulizer of claim 1, wherein the throat of the upstream housing element has an area of at least 30 $mm^2$.

5. The nebulizer of claim 1, wherein the power conductor assembly includes a pair of electrically conductive pins, the pair of electrically conductive pins including a first electrically conductive spring pin in electrical contact with the annular member and a second electrically conductive spring pin in electrical contact with the annular vibration generating element.

6. The nebulizer of claim 1, wherein the downstream housing element includes a protrusion extending in a radial direction and configured to guide engagement of the downstream housing element and the upstream housing element.

7. A nebulizer comprising:

an upstream housing element forming a pin support part, a tubular outlet, and a reservoir upstream of the tubular outlet, the reservoir including a tubular top part, and a funnel-shaped lower part, and an internal surface forming a throat over a vibratable aperture plate;

a reservoir cap upstream of the reservoir of the upstream housing element;

a downstream housing element configured to engage with the upstream housing element;

a pair of electrically conductive spring pins extending through the pin support part of the upstream housing element and configured to convey power to an annular vibration generating element for vibrating the vibratable aperture plate; and an aerosol generator assembly disposed between the upstream housing element and the downstream housing element, the aerosol generator assembly comprising:

an annular member;

the vibratable aperture plate, the vibratable aperture plate including a plurality of apertures;

the annular vibration generating element;

a first sealing member; and a second sealing member, wherein the first sealing member includes a first aperture, an annular portion surrounding the first aperture and extending to a radially outermost edge of the first sealing member, and a second aperture formed in the annular portion, and wherein at least one electrically conductive pin of the pair of electrically conductive pins is axially aligned with the second aperture of the first sealing member.

8. The nebulizer of claim 7, wherein the annular portion of the first sealing member extends beyond the annular vibration generating element in a radial direction.

9. The nebulizer of claim 7, wherein the annular portion of the first sealing member overlaps with and extends beyond the second sealing member in a radial direction.

10. The nebulizer of claim 7, wherein the annular portion of the first sealing member includes a slot on its outer edge.

11. The nebulizer of claim 10, wherein the slot included on the outer edge of the annular portion of the first sealing member engages with the lower housing element.

12. The nebulizer of claim 7, wherein the first sealing member includes a downstream-directed portion that at least partially engages with the annular member.

13. The nebulizer of claim 12, wherein the downstream-directed portion has a depth relative to a body of the first sealing member in a range of 0.5 mm and 1.1 mm.

14. The nebulizer of claim 7, wherein the first sealing member includes a downstream-directed portion that extends entirely around an outer periphery of the annular vibration generating element.

* * * * *